US008338615B2

(12) United States Patent
Gray et al.

(10) Patent No.: US 8,338,615 B2
(45) Date of Patent: *Dec. 25, 2012

(54) HUMAN PROTEIN TYROSINE PHOSPHATASE INHIBITORS AND METHODS OF USE

(75) Inventors: Jeffrey Lyle Gray, Loveland, OH (US); Kande K. D. Amarasinghe, Latham, NY (US); Cynthia Monesa Clark, Concord, MA (US); Ryan Matthew Nichols, Cincinnati, OH (US); Matthew B. Maier, Springboro, OH (US)

(73) Assignee: Aerpio Therapeutics Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/309,452

(22) Filed: Dec. 1, 2011

(65) Prior Publication Data
US 2012/0077853 A1  Mar. 29, 2012

Related U.S. Application Data

(60) Continuation of application No. 12/467,430, filed on May 18, 2009, now Pat. No. 8,188,125, which is a division of application No. 11/821,868, filed on Jun. 26, 2007, now Pat. No. 7,589,212.

(60) Provisional application No. 60/816,825, filed on Jun. 27, 2006.

(51) Int. Cl.
*A61K 31/433* (2006.01)
*C07D 417/12* (2006.01)
(52) U.S. Cl. .................................. 548/138; 514/363
(58) Field of Classification Search .................. 548/138
See application file for complete search history.

(56) References Cited

U.S. PATENT DOCUMENTS

| | | | |
|---|---|---|---|
| 4,673,641 A | 6/1987 | George et al. | |
| 5,424,398 A | 6/1995 | Middeldorp et al. | |
| 5,585,089 A | 12/1996 | Queen et al. | |
| 5,688,781 A | 11/1997 | Siegall et al. | |
| 5,807,819 A | 9/1998 | Cheng et al. | |
| 5,994,128 A | 11/1999 | Fallaux et al. | |
| 6,033,908 A | 3/2000 | Bout et al. | |
| 6,342,219 B1 | 1/2002 | Thorpe et al. | |
| 6,589,758 B1 | 7/2003 | Zhu | |
| 6,596,722 B2 | 7/2003 | Moltzen et al. | |
| 7,226,755 B1 | 6/2007 | Peters et al. | |
| 7,507,568 B2 | 3/2009 | Evdokimov | |
| 7,588,924 B2 | 9/2009 | Evdokiov et al. | |
| 7,589,212 B2 * | 9/2009 | Gray et al. | 548/138 |
| 7,622,593 B2 | 11/2009 | Gray et al. | |
| 7,795,444 B2 * | 9/2010 | Gray et al. | 548/204 |
| 7,973,142 B2 | 7/2011 | Rotello et al. | |
| 8,106,078 B2 * | 1/2012 | Gray et al. | 514/365 |
| 8,188,125 B2 * | 5/2012 | Gray et al. | 514/363 |
| 2004/0167183 A1 | 8/2004 | Klopfenstein et al. | |
| 2004/0204863 A1 | 10/2004 | Kim et al. | |
| 2007/0299116 A1 | 12/2007 | Gray | |
| 2008/0004267 A1 | 1/2008 | Gray | |
| 2008/0076764 A1 | 3/2008 | Peters et al. | |
| 2008/0108631 A1 | 5/2008 | Gray et al. | |
| 2009/0227639 A1 | 9/2009 | Gray et al. | |

FOREIGN PATENT DOCUMENTS

| | | |
|---|---|---|
| WO | WO 00/65085 | 11/2000 |
| WO | WO 00/65088 | 11/2000 |
| WO | WO 02/26774 | 4/2002 |
| WO | WO 2011/005330 | 1/2011 |

OTHER PUBLICATIONS

U.S. Appl. No. 11/823,086, filed Jun. 26, 2007, Gray, Restriction Requirement, Oct. 2, 2008.
U.S. Appl. No. 11/823,086, filed Jun. 26, 2007, Gray, Response to Restriction Requirement, Dec. 2, 2008.
U.S. Appl. No. 11/823,086, filed Jun. 26, 2007, Gray, Preliminary Amendment, Jan. 20, 2009.
U.S. Appl. No. 11/823,086, filed Jun. 26, 2007, Gray, Non-Final Office Action, Mar. 4, 2009.
U.S. Appl. No. 11/823,086, filed Jun. 26, 2007, Gray, Amendment and Response to Office Action, Apr. 30, 2009.
U.S. Appl. No. 11/823,086, filed Jun. 26, 2007, Gray, Final Rejection, Sep. 2, 2009.
U.S. Appl. No. 11/823,086, filed Jun. 26, 2007, Gray, Amendment After Final, Sep. 11, 2009.
U.S. Appl. No. 11/823,086, filed Jun. 26, 2007, Gray, Notice of Allowance, Sep. 22, 2009.
U.S. Appl. No. 11/821,846, filed Jun. 26, 2007, Gray, Preliminary Amendment, Feb. 15, 2010.
U.S. Appl. No. 11/821,846, filed Jun. 26, 2007, Gray, Restriction Requirement (telephonic), Apr. 12, 2010.
U.S. Appl. No. 11/821,846, filed Jun. 26, 2007, Gray, Non-Final Office Action, Apr. 23, 2010.
U.S. Appl. No. 11/821,846, filed Jun. 26, 2007, Gray, Amendment and Response to Office Action, Jun. 8, 2010.
U.S. Appl. No. 11/821,846, filed Jun. 26, 2007, Gray, Notice of Allowance, Jul. 26, 2010.
U.S. Appl. No. 12/850,026, filed Aug. 4, 2011, Gray, Non-Final Office Action, Aug. 8, 2011.
U.S. Appl. No. 12/850,026, filed Aug. 4, 2011, Gray, Response to Office Action, Aug. 30, 2011.
U.S. Appl. No. 12/850,026, filed Aug. 4, 2011, Gray, Final Office Action, Oct. 24, 2011.
U.S. Appl. No. 12/850,026, filed Aug. 4, 2011, Gray, Response to Final Office Action, Nov. 1, 2011.
U.S. Appl. No. 12/850,026, filed Aug. 4, 2011, Gray, Notice of Allowance, Nov. 15, 2011.
U.S. Appl. No. 11/821,868, filed Jun. 26, 2007, Gray, Restriction Requirement, Mar. 27, 2008.
U.S. Appl. No. 11/821,868, filed Jun. 26, 2007, Gray, Response to Restriction Requirement, Jun. 26, 2008.
U.S. Appl. No. 11/821,868, filed Jun. 26, 2007, Gray, Non-Final Office Action, Oct. 2, 2008.

(Continued)

*Primary Examiner* — Laura L. Stockton
(74) *Attorney, Agent, or Firm* — Richard S. Echler

(57) ABSTRACT

The present disclosure relates to compounds effective as human protein tyrosine phosphatase beta (HPTP-β) inhibitors thereby regulating angiogenesis. The present disclosure further relates to compositions comprising one or more human protein tyrosine phosphatase beta (HPTP-β) inhibitors, and to methods for regulating angiogenesis.

11 Claims, No Drawings

OTHER PUBLICATIONS

U.S. Appl. No. 11/821,868, filed Jun. 26, 2007, Gray, Amendment and Response to Office Action, Nov. 3, 2008.
U.S. Appl. No. 11/821,868, filed Jun. 26, 2007, Gray, Final Office Action, Jan. 9, 2009.
U.S. Appl. No. 11/821,868, filed Jun. 26, 2007, Gray, Amendment After Final Rejection, Mar. 9, 2009.
U.S. Appl. No. 11/821,868, filed Jun. 26, 2007, Gray, Notice of Allowance, Mar. 25, 2009.
U.S. Appl. No. 11/821,868, filed Jun. 26, 2007, Gray, Amendment After Final and Response to Office Action, Apr. 21, 2009.
U.S. Appl. No. 11/821/868, filed Jun. 26, 2007, Gray, Issue Notification, Jun. 3, 2009.
U.S. Appl. No. 11/821,868, filed Jun. 18, 2009, Gray, Petition for Withdrawal from Issue, Jun. 18, 2009.
U.S. Appl. No. 11/821,868, filed Jun. 18, 2009, Gray, Request for Continued Examination, Jun. 18, 2009.
U.S. Appl. No. 11/821,868, filed Jun. 18, 2009, Gray, Information Disclosure Statement, Jun. 18, 2009.
U.S. Appl. No. 11/821,868, filed Jun. 18, 2009, Gray, Notice of Allowance, Jul. 28, 2009.
U.S. Appl. No. 12/467,430, filed May 18, 2009, Gray, Restriction Requirement, Jun. 28, 2011.
U.S. Appl. No. 12/467,430, filed May 18, 2009, Gray, Response to Restriction Requirement, Jul. 8, 2011.
U.S. Appl. No. 12/467,430, filed May 18, 2009, Gray, Non-Final OA, Oct. 17, 2011.
U.S. Appl. No. 12/467,430, filed May 18, 2009, Gray, Amendment/Response to OA, Oct. 18, 2011.
U.S. Appl. No. 12/467,430, filed May 18, 2009, Gray, Final OA, Dec. 6, 2011.
U.S. Appl. No. 12/467,430, filed May 18, 2009, Gray, Terminal Disclaimer Filed, Dec. 9, 2011.
U.S. Appl. No. 12/467,430, filed May 18, 2009, Gray, Response to Final OA, Jan. 23, 2012.
U.S. Appl. No. 12/467,430, filed May 18, 2009, Gray, Terminal Disclaimer Filed, Feb. 3, 2012.
U.S. Appl. No. 12/467,430, filed May 18, 2009, Gray, Response to Final OA, Feb. 3, 2012.
U.S. Appl. No. 12/467,430, filed May 18, 2009, Gray, Advisory Action, Mar. 2, 2012.
U.S. Appl. No. 12/467,430, filed May 18, 2009, Gray, Notice of Allowance, Mar. 12, 2012.
U.S. Appl. No. 12/467,430, filed May 18, 2009, Gray, Issue Notification, May 10, 2012.
U.S. Appl. No. 10/633,742, filed Aug. 4, 2003, Peters, Requirement for Restriction/Election, Feb. 9, 2006.
U.S. Appl. No. 10/633,742, filed Aug. 4, 2003, Peters, Response to Election / Restriction, Mar. 6, 2006.
U.S. Appl. No. 10/633,742, filed Aug. 4, 2003, Peters, Non-Final Rejection, May 1, 2006.
U.S. Appl. No. 10/633,742, filed Aug. 4, 2003, Peters, Amendment/Request Reconsideration After Non-Final Rejection, Oct. 31, 2006.
U.S. Appl. No. 10/633,742, filed Aug. 4, 2003, Peters, Supplemental Response or Supplemental Amendment, Jan. 19, 2007.
U.S. Appl. No. 10/633,742, filed Aug. 4, 2003, Peters, Notice of Allowance, Feb. 6, 2007.
U.S. Appl. No. 10/633,742, filed Aug. 4, 2003, Peters, Issue Notification, May 16, 2007.
U.S. Appl. No. 10/633,742, filed Aug. 4, 2003, Peters, Request for Certificate of Correction, Apr. 10, 2008.
U.S. Appl. No. 10/633,742, filed Aug. 4, 2003, Peters, Certificate of Correction—Post Issue Communication, Apr. 22, 2008.
U.S. Appl. No. 10/633,742, filed Aug. 4, 2003, Peters, Certificate of Correction—Post Issue Communication, May 20, 2008.
U.S. Appl. No. 11/787,535, filed Apr. 17, 2007, Peters et al., Non-Final OA, Mar. 25, 2008.
U.S. Appl. No. 11/787,535, filed Apr. 17, 2007, Peters et al., Amendment and Response, Sep. 17, 2008.
U.S. Appl. No. 11/787,535, filed Apr. 17, 2007, Peters et al., Final OA, Jan. 8, 2009.
U.S. Appl. No. 11/787,535, filed Apr. 17, 2007, Peters et al., Amendment After Final OA, Mar. 12, 2009.
U.S. Appl. No. 11/787,535, filed Apr. 17, 2007, Peters et al., Advisory Action, Apr. 15, 2009.
U.S. Appl. No. 11/787,535, filed Apr. 17, 2007, Peters et al., Amendment and RCE, May 7, 2009.
U.S. Appl. No. 11/787,535, filed Apr. 17, 2007, Peters et al., Notice of Allowance, Aug. 11, 2009.
U.S. Appl. No. 12/610,843, filed Nov. 2, 2009, Peters et al., Restriction Requirement, May 27, 2010.
U.S. Appl. No. 12/610,843, filed Nov. 2, 2009, Peters et al., Response to Restriction Requirement, Jun. 24, 2010.
U.S. Appl. No. 12/610,843, filed Nov. 2, 2009, Peters et al., Non-Final OA, Sep. 13, 2010.
U.S. Appl. No. 12/610,843, filed Nov. 2, 2009, Peters et al., Amendment/Response to OA, Mar. 5, 2011.
U.S. Appl. No. 12/610,843, filed Nov. 2, 2009, Peters et al., Final OA, Apr. 29, 2011.
U.S. Appl. No. 12/610,843, filed Nov. 2, 2009, Peters et al., Amemedment/Request for Continued Examination, Oct. 27, 2011.
U.S. Appl. No. 10/634,027, filed Aug. 4, 2003, Evdokimov, Restriction Requirement, Jan. 19, 2006.
U.S. Appl. No. 10/634,027, filed Aug. 4, 2003, Evdokimov, Response to Restriction Requirement, Feb. 13, 2006.
U.S. Appl. No. 10/634,027, filed Aug. 4, 2003, Evdokimov, Non-Final Office Action, Apr. 13, 2006.
U.S. Appl. No. 10/634,027, filed Aug. 4, 2003, Evdokimov, Reply After 1st Office Action, Oct. 16, 2006.
U.S. Appl. No. 10/634,027, filed Aug. 4, 2003, Evdokimov, Final Office Action, Nov. 22, 2006.
U.S. Appl. No. 10/634,027, filed Aug. 4, 2003, Evdokimov, Amendment After Final Office Action, May 21, 2007.
U.S. Appl. No. 10/634,027, filed Aug. 4, 2003, Evdokimov, Non-Final Office Action, Jun. 12, 2007.
U.S. Appl. No. 10/634,027, filed Aug. 4, 2003, Evdokimov, Amendment in Response to Non-Final Office Action, Sep. 17, 2007.
U.S. Appl. No. 10/634,027, filed Aug. 4, 2003, Evdokimov, Final Office Action, Nov. 9, 2007.
U.S. Appl. No. 10/634,027, filed Aug. 4, 2003, Evdokimov, Amendment and Response to Final Office Action, May 8, 2008.
U.S. Appl. No. 10/634,027, filed Aug. 4, 2003, Evdokimov, Non-Final Office Action, Jun. 17, 2008.
U.S. Appl. No. 10/634,027, filed Aug. 4, 2003, Evdokimov, Amendment and Response to Non-Final Office Action, Sep. 16, 2008.
U.S. Appl. No. 10/634,027, filed Aug. 4, 2003, Evdokimov, Notice of Allowance, Jan. 14, 2009.
U.S. Appl. No. 10/634,027, filed Aug. 4, 2003, Evdokimov, Issue Notification, Mar. 4, 2009.
U.S. Appl. No. 10/634,027, filed Aug. 4, 2003, Evdokimov, Certificate of Correction, May 26, 2009.
U.S. Appl. No. 12/409,111, filed Mar. 23, 2009, Evdokimov, Applicant Interview Summary, Mar. 15, 2010.
U.S. Appl. No. 12/409,111, filed Mar. 23, 2009, Evdokimov, Examiner Interview Summary, Mar. 15, 2010.
U.S. Appl. No. 12/409,111, filed Mar. 23, 2009, Evdokimov, Terminal Disclaimer, Apr. 12, 2010.
U.S. Appl. No. 12/409,111, filed Mar. 23, 2009, Evdokimov, Notice of Allowance, Apr. 27, 2010.
U.S. Appl. No. 12/677,512, filed Mar. 22, 2010, Shalwitz, Restriction Requirement, Jan. 26, 2012.
U.S. Appl. No. 12/677,512, filed Mar. 22, 2010, Shalwitz, Response to Restriction Requirement, Feb. 1, 2012.
U.S. Appl. No. 12/677,512, filed Mar. 22, 2010, Shalwitz, $2^{nd}$ Restriction Requirement, Apr. 5, 2012.
U.S. Appl. No. 12/677,512, filed Mar. 22, 2010, Shalwitz, $2^{nd}$ Response to $2^{nd}$ Restriction Requirement, Jul. 13, 2012.
U.S. Appl. No. 11/784,094, filed Apr. 5, 2007, Rotello, Restriction Requirement, Jul. 23, 2009.
U.S. Appl. No. 11/784,094, filed Apr. 5, 2007, Rotello, Response to Restriction Requirement, Jul. 29, 2009.
U.S. Appl. No. 11/784,094, field Apr. 5, 2007, Rotello, Notice to Comply: Sequence Listing, Nov. 23, 2009.
U.S. Appl. No. 11/784,094, filed Apr. 5, 2007, Rotello, Response to Notice, Jan. 25, 2010.

U.S. Appl. No. 11/784,094, filed Apr. 5, 2007, Rotello, Non-Final Office Action, May 5, 2010.
U.S. Appl. No. 11/784,094, filed Apr. 5, 2007, Rotello, Reply After 1st Office Action, Jul. 1, 2010.
U.S. Appl. No. 11/784,094, filed Apr. 5, 2007, Rotello, Non-Final Office Action, Sep. 17, 2010.
U.S. Appl. No. 11/784,094, filed Apr. 5, 2007, Rotello, Response to Office Action, Jan. 18, 2011.
U.S. Appl. No. 11/784,094, filed Apr. 5, 2007, Rotello, Final Office Action, Apr. 4, 2011.
U.S. Appl. No. 11/784,094, filed Apr. 5, 2007, Rotello, Amendment/Response After Final, Apr. 26, 2011.
U.S. Appl. No. 11/784,094, filed Apr. 5, 2007, Rotello, Notice of Allowance, May 19, 2011.
U.S. Appl. No. 11/784,094, filed Apr. 5, 2007, Rotello, Issue Notification, Jun. 15, 2011.
PCT, PCT/US2007/014822, Jun. 27, 2007, Aerpio Therapeutics, Written Opinion, Dec. 27, 2008.
PCT, PCT/US2007/014822, Jun. 27, 2007, Aerpio Therapeutics, International Search Report, Feb. 14, 2008.
PCT, PCT/US2007/014822, Jun. 27, 2007, Aeprio Therapeutics, International Preliniminary Report on Patentability, Jan. 6, 2009.
PCT, PCT/US2007/014823, Jun. 27, 2007, Aerpio Therapeutics, International Search Report, Oct. 12, 2007.
PCT, PCT/US2007/014823, Jun. 27, 2007, Aerpio Therapeutics, Written Opinion, Oct. 12, 2007.
PCT, PCT/US2007/014823, Jun. 27, 2007, Aerpio Therapeutics, Response to Search Report and Amendment, Feb. 8, 2008.
PCT, PCT/US2007/014823, Jun. 27, 2007, Aerpio Therapeutics, International Preliminary Report on Patentability, Jan. 6, 2009.
PCT, PCT/US2007/014824, Jun. 27, 2007, Aerpio Therapeutics, Written Opinion, Nov. 12, 2007.
PCT, PCT/US2007/014824, Jun. 27, 2007, Aerpio Therapeutics, Response to Search Report and Amendment, Feb. 8, 2008.
PCT, PCT/US2007/014824, Jun. 27, 2007, Aerpio Therapeutics, International Search Report, Feb. 14, 2008.
PCT, PCT/US2007/014824, Jun. 27, 2007, Aerpio Therapeutics, International Preliminary Report on Patentability, Jan. 6, 2009.
PCT, PCT/US2010/020817, Jan. 12, 2010, Aerpio Therapeutics, International Search Report, Mar. 30, 2010.
PCT, PCT/US2010/020822, Jan. 12, 2010, Aerpio Therapeutics, International Search Report, Mar. 30, 2010.
PCT, PCT/US2011/054873, Oct. 5, 2011, Aerpio Therapeutics, International Search Report, Mar. 26, 2012.
AU, 2007265453, Jun. 27, 2007, Aerpio Therapeutics, Examiner's Report, Dec. 15, 2010.
AU, 2007265453, Jun. 27, 2007, Aerpio Therapeutics, Response to Examiner's Report, Feb. 8, 2011.
AU, 2007265453, Jun. 27, 2007, Aerpio Therapeutics, Examiner's Report, May 10, 2011.
AU, 2007265453, Jun. 27, 2007, Aerpio Therapeutics, Response to Examiner's Report, Aug. 1, 2011.
AU, 2007265453, Jun. 27, 2007, Aerpio Therapeutics, Examiner's Report, Oct. 26, 2011.
AU, 2007265453, Jun. 27, 2007, Aerpio Therapeutics, Response to Examiner's Report, Nov. 23, 2011.
AU, 2007265453, Jun. 27, 2007, Aerpio Therapeutics, Notice of Acceptance, Dec. 21, 2011.
CA, 2,657,096, Jun. 27, 2007, Aerpio Therapeutics, Examiner's Report, May 25, 2011.
CA, 2,657,096, Jun. 27, 2007, Aerpio Therapeutics, Response to Examiner's Report, Jun. 20, 2011.
CA, 2,657,096, Jun. 27, 2007, Aerpio Therapeutics, Examiner's Report, Feb 27, 2012.
CA, 2,657,096, Jun. 27, 2007, Aerpio Therapeutics, Response to Examiner's Report, Jul. 6, 2012.
CN, 200780030939.0, Jun. 27, 2007, Aerpio Therapeutics, Examiner's Report, May 11, 2011.
CN, 200780030939.0, Jun. 27, 2007, Aerpio Therapeutics, Response to Examiner's Report, Jul. 12, 2011.
EP, 07 809 907.4, Jun. 27, 2007, Aerpio Therapeutics, Examination Report, Nov. 30, 2010.
EP, 07 809 907.4, Jun. 27, 2007, Aerpio Therapeutics, Respoonse to Examination Report, Jan. 19, 2011.
EP, 07 809 907.4, Jun. 27, 2007, Aerpio Therapeutics, Remarks from foreign associate, Mar. 28, 2011.
EP, 07 809 907.4, Jun. 27, 2007, Aerpio Therapeutics, $2^{nd}$ Response to Examination Report, Mar. 30, 2011.
ID, W-00200804210, Jun. 27, 2007, Aerpio Therapeutics, Examination Report, Feb. 18, 2011.
ID, W-00200804210, Jun. 27, 2007, Aerpio Therapeutics, Response to Examination Report, Jul. 5, 2011.
IL, 196128, Jun. 27, 2007, Aerpio Therapeutics, Examination Report, Mar. 23, 2010.
IL, 196128, Jun. 27, 2007, Aerpio Therapeutics, Response to Examination Report, May 13, 2010.
IL, 196128, Jun. 27, 2007, Aerpio Therapeutics, Remarks from foreign associate, May 6, 2010.
IL, 196128, Jun. 27, 2007, Aerpio Therapeutics, $2^{nd}$ Response to Examination Report, Jul. 14, 2010.
IL, 196128, Jun. 27, 2007, Aerpio Therapeutics, Office Action, Mar. 22, 2012.
IL, 196128, Jun. 27, 2007, Aerpio Therapeutics, Response to Office Action, May 23, 2012.
JP, 2009-518226, Jun. 27, 2007, Aerpio Therapeutics, Examination Report, May 30, 2012.
JP, 2009-518226, Jun. 27, 2007, Aerpio Therapeutics, Response to Examination Report, Jul. 5, 2012.
KR, 2009-7001678, Jun. 27, 2007, Aerpio Therapeutics, Office Action, Apr. 6, 2011.
KR, 2009-7001678, Jun. 27, 2007, Aerpio Therapeutics, Response to Office Action and Amendment, May 31, 2011.
KR, 2009-7001678, Jun. 27, 2007, Aerpio Therapeutics, Final Office Action, Dec. 24, 2011.
KR, 2009-7001678, Jun. 27, 2007, Aerpio Therapeutics, Response to Final Office Action, Dec. 29, 2011.
KR, 2009-7001678, Jun. 27, 2007, Aerpio Therapeutics, Notice of Allowance, Jun. 5, 2012.
NZ, 574407, Jun. 27, 2007, Aerpio Therapeutics, Examination Report, Jun. 14, 2010.
NZ, 574407, Jun. 27, 2007, Aerpio Therapeutics, Response to Examination Report, Jul. 1, 2010.
NZ, 574407, Jun. 27, 2007, Aerpio Therapeutics, Remarks for foreign associate, Apr. 19, 2011.
NZ, 574407, Jun. 27, 2007, Aerpio Therapeutics, $2^{nd}$ Response to Examination Report, Apr. 21, 2011.
NZ, 574407, Jun. 27, 2007, Aerpio Therapeutics, Remarks for foreign associate, Apr. 28, 2011.
NZ, 574407, Jun. 27, 2007, Aerpio Therapeutics, $3^{rd}$ Response to Examination Report, May 3, 2011.
NZ, 574407, Jun. 27, 2007, Aerpio Therapeutics, $2^{nd}$ Examination Report, Jun. 2, 2011.
NZ, 574407, Jun. 27, 2007, Aerpio Therapeutics, Response to Examination Report, Jul. 21, 2011.
NZ, 574407, Jun. 27, 2007, Aerpio Therapeutics, $3^{rd}$ Examination Report, Sep. 16, 2011.
NZ, 574407, Jun. 27, 2007, Aerpio Therapeutics, Response to Examination Report, Oct. 25, 2011.
NZ, 574407, Jun. 27, 2007, Aerpio Therapeutics, $4^{th}$ Examination Report, Nov. 30, 2011.
NZ, 574407, Jun. 27, 2007, Aerpio Therapeutics, Response to Examination Report, Dec. 14, 2011.
PH, 1-2009-500031, Jun. 27, 2007, Aerpio Therapeutics, Examination Report, Mar. 15, 2012.
PH, 1-2009-500031, Jun. 27, 2007, Aerpio Therapeutics, Response to Examination Report, Jun. 12, 2012.
PH, 1-2009-500031, Jun. 27, 2007, Aerpio Therapeutics, Notice of Allowance, Jun. 15, 2012.
RU, 2009102516, Jun. 27, 2007, Aerpio Therapeutics, Office Action, Apr. 7, 2010.
RU, 2009102516, Jun. 27, 2007, Aerpio Therapeutics, Response to Office Action and Amendment, May 4, 2010.
RU, 2009102516, Jun. 27, 2007, Aerpio Therapeutics, $2^{nd}$ Examination Report, Aug. 23, 2010.

RU, 2009102516, Jun. 27, 2007, Aerpio Therapeutics, Response to 2$^{nd}$ Examination Report, Sep. 7, 2010.
RU, 2009102516, Jun. 27, 2007, Aerpio Therapeutics, 3$^{rd}$ Examination Report, Dec. 14, 2010.
RU, 2009102516, Jun. 27, 2007, Aerpio Therapeutics, Response to 3$^{rd}$ Examination Report, Dec. 29, 2010.
RU, 2009102516, Jun. 27, 2007, Aerpio Therapeutics, Claims Amendments in Response to Interview, Jul. 21, 2011.
RU, 2009102516, Jun. 27, 2007, Aerpio Therapeutics, Decision to Grant, Oct. 27, 2011.
SG, 200809619-0, Jun. 27, 2007, Aerpio Therapeutics, Written Opinion, Dec. 28, 2009.
SG, 200809619-0, Jun. 27, 2007, Aerpio Therapeutics, Response to Written Opinion and Amendment, Jan. 27, 2010.
SG, 200809619-0, Jun. 27, 2007, Aerpio Therapeutics, Response to Written Opinion and Amendment, Jan. 10, 2011.
SG, 200809619-0, Jun. 27, 2007, Aerpio Therapeutics, Notice of Allowance, Jun. 6, 2011.
AU, 2007265454, Jun. 27, 2007, Aerpio Therapeutics, Preliminary Amendment, Feb. 25, 2010.
AU, 2007265454, Jun. 27, 2007, Aerpio Therapeutics, 1$^{st}$ Office Action, Feb. 25, 2011.
AU, 2007265454, Jun. 27, 2007, Aerpio Therapeutics, Response to 1$^{st}$ Office Action, Mar. 25, 2011.
AU, 2007265454, Jun. 27, 2007, Aerpio Therapeutics, 2$^{nd}$ Office Action, Jul. 25, 2011.
AU, 2007265454, Jun. 27, 2007, Aerpio Therapeutics, Response to 2$^{nd}$ Office Action, Aug. 29, 2011.
AU, 2007265454, Jun. 27, 2007, Aerpio Therapeutics, Notice of Acceptance, Nov. 16, 2011.
CA, 2,657,107, Jun. 27, 2007, Aerpio Therapeutics, 1$^{st}$ Office Action, May 25, 2011.
CA, 2,657,107, Jun. 27, 2007, Aerpio Therapeutics, Response to 1$^{st}$ Office Action, Jun. 21, 2011.
CA, 2,657,107, Jun. 27, 2007, Aerpio Therapeutics, 2$^{nd}$ Office Action, Mar. 7, 2012.
CA, 2,657,107, Jun. 27, 2007, Aerpio Therapeutics, Response to 2$^{nd}$ Office Action, May 10, 2012.
CN, 200780030984.6, Jun. 27, 2007, Aerpio Therapeutics, 1$^{st}$ Office Action, Nov. 3, 2010.
CN, 200780030984.6, Jun. 27, 2007, Aerpio Therapeutics, Response to 1$^{st}$ Office Action, Dec. 16, 2010.
CN, 200780030984.6, Jun. 27, 2007, Aerpio Therapeutics, 2$^{nd}$ Office Action, May 30, 2011.
CN, 200780030984.6, Jun. 27, 2007, Aerpio Therapeutics, Response to 2$^{nd}$ Office Action, Jul. 13, 2011.
CN, 200780030984.6, Jun. 27, 2007, Aerpio Therapeutics, Further Response to 2$^{nd}$ Office Action, Aug. 15, 2011.
CN, 200780030984.6, Jun. 27, 2007, Aerpio Therapeutics, 3$^{rd}$ Office Action, May 23, 2012.
CN, 200780030984.6, Jun. 27, 2007, Aerpio Therapeutics, Response to 3$^{rd}$ Office Action, Aug. 2, 2012.
EP, 07 809 908.2, Jun. 27, 2007, Aerpio Therapeutics, Preliminary Amendment, Feb. 25, 2010.
EP, 07 809 908.2, Jun. 27, 2007, Aerpio Therapeutics, 1$^{st}$ Office Action, Nov. 30, 2010.
EP, 07 809 908.2, Jun. 27, 2007, Aerpio Therapeutics, Response to 1$^{st}$ Office Action, Jan. 11, 2011.
EP, 07 809 908.2, Jun. 27, 2007, Aerpio Therapeutics, Further Response to 1$^{st}$ Office Action, Apr. 4, 2011.
ID, W-00200804213, Jun. 27, 2007, Aerpio Therapeutics, 1$^{st}$ Office Action, May 26, 2011.
ID, W-00200804213, Jun. 27, 2007, Aerpio Therapeutics, Response to 1$^{st}$ Office Action, Aug. 2, 2011.
IL, 196129, Jun. 27, 2007, Aerpio Therapeutics, 1$^{st}$ Office Action, Mar. 22, 2012.
IL, 196129, Jun. 27, 2007, Aerpio Therapeutics, Response to 1$^{st}$ Office Action, May 28, 2012.
JP, 2009-518227, Jun. 27, 2007, Aerpio Therpeutics, Preliminary Amendment, Feb. 23, 2010.
KR, 2009-7001694, Jun. 27, 2007, Aerpio Therapeutics, Preliminary Amendment, Feb. 25, 2010.
KR, 2009-7001694, Jun. 27, 2007, Aerpio Therapeutics, 1$^{st}$ Office Action, Apr. 19, 2011.
KR, 2009-7001694, Jun. 27, 2007, Aerpio Therapeutics, Response to 1$^{st}$ Office Action, Jun. 9, 2011.
KR, 2009-7001694, Jun. 27, 2007, Aerpio Therapeutics, Further Response to 1$^{st}$ Office Action, Sep. 19, 2011.
KR, 2009-7001694, Jun. 27, 2007, Aerpio Therapeutics, Further Response to 1$^{st}$ Office Action, Oct. 17, 2011.
KR, 2009-7001694, Jun. 27, 2007, Aerpio Therapeutics, Final Rejection, Mar. 15, 2012.
KR, 2009-7001694, Jun. 27, 2007, Aerpio Therapeutics, Appreal to Tribunal, Jul. 5, 2012.
MX, MX/A/2009/000289, Jun. 27, 2007, Aerpio Therapeutics, Preliminary Amendment, Mar. 1, 2010.
MX, MX/A/2009/000289, Jun. 27, 2007, Aerpio Therapeutics, 1$^{st}$ Office Action, Apr. 23, 2012.
MX, MX/A/2009/000289, Jun. 27, 2007, Aerpio Therapeutics, Response to 1$^{st}$ Office Action, Apr. 25, 2012.
MX, MX/A/2009/000289, Jun. 27, 2007, Aerpio Therapeutics, Further Response to 1$^{st}$ Office Action, May 7, 2012.
NZ, 574406, Jun. 27, 2007, Aerpio Therapeutics, Preliminary Amendment, Mar. 1, 2010.
NZ, 574406, Jun. 27, 2007, Aerpio Therapeutics, 1$^{st}$ Office Action, Jun. 14, 2010.
NZ, 574406, Jun. 27, 2007, Aerpio Therapeutics, Response to 1$^{st}$ Office Action, Jul. 7, 2010.
NZ, 574406, Jun. 27, 2007, Aerpio Therapeutics, Further Response to 1$^{st}$ Office Action, Apr. 25, 2011.
NZ, 574406, Jun. 27, 2007, Aerpio Therapeutics, Further Response to 1$^{st}$ Office Action, Aug. 31, 2011.
NZ, 574406, Jun. 27, 2007, Aerpio Therapeutics, 2$^{nd}$ Office Action, Sep. 20, 2011.
NZ, 574406, Jun. 27, 2007, Aerpio Therapeutics, Response to 2$^{nd}$ Office Action, Dec. 20, 2011.
NZ, 574406, Jun. 27, 2007, Aerpio Therapeutics, Patent Grant, May 7, 2011.
PH, 1-2009-500032, Jun. 27, 2007, Aerpio Therapeutics, Office Action, Apr. 27, 2012.
PH, 1-2009-500032, Jun. 27, 2007, Aerpio Therapeutics, Response to Office Action, Jun. 5, 2012.
PH, 1-2009-500032, Jun. 27, 2007, Aerpio Therapeutics, Allowance, Jul. 5, 2012.
RU, 2009102538, Jun. 27, 2007, Aerpio Therapeutics, Preliminary Amendment, Mar. 6, 2009.
RU, 2009102538, Jun. 27, 2007, Aerpio Therapeutics, 1$^{st}$ Office Action, Oct. 15, 2010.
RU, 2009102538, Jun. 27, 2007, Aerpio Therapeutics, Response to 1$^{st}$ Office Action, Oct. 27, 2010.
RU, 2009102538, Jun. 27, 2007, Aerpio Therapeutics, 2$^{nd}$ Office Action, Apr. 28, 2011.
RU, 2009102538, Jun. 27, 2007, Aerpio Therapeutics, Response to 2$^{nd}$ Office Action, May 4, 2011.
RU, 2009102538, Jun. 27, 2007, Aerpio Therapeutics, 3$^{rd}$ Office Action, May 27, 2011.
RU, 2009102538, Jun. 27, 2007, Aerpio Therapeutics, Response to 3$^{rd}$ Office Action, May 27, 2011.
RU, 2009102538, Jun. 27, 2007, Aerpio Therapeutics, Decision to Grant, Jun. 2, 2011.
SG, 200809621-6, Jun. 27, 2007, Aerpio Therapeutics, Written Opinion, Dec. 7, 2009.
SG, 200809621-6, Jun. 27, 2007, Aerpio Therapeutics, Response to Written Opinion and Amendment, Feb. 19, 2010.
SG, 200809621-6, Jun. 27, 2007, Aerpio Therapeutics, 2$^{nd}$ Written Opinion, Sep. 16, 2010.
SG, 200809621-6, Jun. 27, 2007, Aerpio Therapeutics, Response to 2$^{nd}$ Written Opinion and Amendment, Nov. 16, 2010.
SG, 200809621-6, Jun. 27, 2007, Aerpio Therapeutics, Patent Issued, Jul. 29, 2011.
ZA, 2009-00492, Jun. 27, 2007, Aerpio Therapeutics, Amendment, Feb. 25, 2010.
AU, 2007265455, Jun. 27, 2007, Aerpio Therapeutics, Examination Report, Feb. 8, 2011.

AU, 2007265455, Jun. 27, 2007, Aerpio Therapeutics, Response to Examination Report, Oct. 13, 2011.
AU, 2007265455, Jun. 27, 2007, Aerpio Therapeutics, Notice of Acceptance, Oct. 31, 2011.
AU, 2012200253, Jan. 16, 2010, Aerpio Therapeutics, Office Action, Apr. 16, 2012.
AU, 2012200253, Jan. 16, 2010, Aerpio Therapeutics, Response to Office Action, Jun. 12, 2012.
AU, 2012200253, Jan. 16, 2010, Aerpio Therapeutics, Notice of Acceptance, Jul. 5, 2012.
CA, 2,656,915, Jun. 27, 2007, Aerpio Therapeutics, Office Action, Oct. 26, 2011.
CA, 2,656,915, Jun. 27, 2007, Aerpio Therapeutics, Response to Office Action, Jan. 9, 2012.
CA, 2,656,915, Jun. 27, 2007, Aerpio Therapeutics, Notice of Allowance, Apr. 18, 2012.
CN, 200780031040.0, Jun. 27, 2007, Aerpio Therapeutics, Office Action, Mar. 23, 2011.
CN, 200780031040.0, Jun. 27, 2007, Aerpio Therapeutics, Response to Office Action, Jul. 7, 2011.
CN, 200780031040.0, Jun. 27, 2007, Aerpio Therapeutics, Further Response to Office Action, Aug. 5, 2011.
CN, 200780031040.0, Jun. 27, 2007, Aerpio Therapeutics, Office Action, Sep. 22, 2011.
CN, 200780031040.0, Jun. 27, 2007, Aerpio Therapeutics, Response to Office Action, Nov. 4, 2011.
CN, 200780031040.0, Jun. 27, 2007, Aerpio Therapeutics, Further Response to Office Action, Dec. 6, 2011.
CN, 200780031040.0, Jun. 27, 2007, Aerpio Therapeutics, Notice of Allowance, Jan. 19, 2012.
EP, 07 809 909.0, Jun. 27, 2009, Aerpio Therapeutics, Office Action, Nov. 30, 2010.
EP, 07 809 909.0, Jun. 27, 2009, Aerpio Therapeutics, Response to Office Action, Jan. 14, 2011.
EP, 07 809 909.0, Jun. 27, 2009, Aerpio Therapeutics, Further Response to Office Action, Nov. 27, 2011.
KR, 2009-7001692, Jun. 27, 2007, Aerpio Therapeutics, Office Action, May 14, 2011.
KR, 2009-7001692, Jun. 27, 2007, Aerpio Therapeutics, Response to Office Action, Sep. 16, 2011.
KR, 2009-7001692, Jun. 27, 2007, Aerpio Therapeutics, Further Response to Office Action, Feb. 16, 2012.
KR, 2009-7001692, Jun. 27, 2007, Aerpio Therapeutics, Notice of Allowance, Jun. 13, 2012.
MX, MX/A/2009/000290, Jun. 27, 2007, Aerpio Therapeutics, Office Action, May 25, 2010.
MX, MX/A/2009/000290, Jun. 27, 2007, Aerpio Therapeutics, Response to Office Action, Jul. 27, 2010.
MX, MX/A/2009/000290, Jun. 27, 2007, Aerpio Therapeutics, Notice of Allowance, Aug. 27, 2011.
NZ, 574405, Jun. 27, 2007, Aerpio Therapeutics, Examination Report, Jun. 14. 2010.
NZ, 574405, Jun. 27, 2007, Aerpio Therapeutics, Response to Examination Report, May 16, 2011.
NZ, 574405, Jun. 27, 2007, Aerpio Therapeutics, $2^{nd}$ Examination Report, Jun. 2, 2011.
NZ, 574405, Jun. 27, 2007, Aerpio Therapeutics, Response to Examination Report, Sep. 11, 2011.
NZ, 574405, Jun. 27, 2007, Aerpio Therapeutics, $3^{rd}$ Examination Report, Oct. 4, 2011.
NZ, 574405, Jun. 27, 2007, Aerpio Therapeutics, Response to Examination Report, Dec. 5, 2011.
PH, 1-2009-500033, Jun. 27, 2007, Aerpio Therapeutics, Office Action, Apr. 25, 2012.
PH, 1-2009-500033, Jun. 27, 2007, Aerpio Therapeutics, Response to Office Action, May 10, 2012.
RU, 2009102537, Jun. 27, 2007, Aerpio Therapeutics, Office Action, Oct. 21, 2010.
RU, 2009102537, Jun. 27, 2007, Aerpio Therapeutics, Response to Office Action, Nov. 3, 2010.
RU, 2009102537, Jun. 27, 2007, Aerpio Therapeutics, Further Response to Office Action, Dec. 17, 2010.
RU, 2009102537, Jun. 27, 2007, Aerpio Therapeutics, Decision to Grant, May 10, 2011.
SG, 200909622-4, Jun. 27, 2007, Aerpio Therapeutics, Written Opinion, Dec. 7, 2009.
SG, 200909622-4, Jun. 27, 2007, Aerpio Therapeutics, Response to Written Opinion and Amendment, Feb. 19, 2010.
SG, 200909622-4, Jun. 27, 2007, Aerpio Therapeutics, Notice of allowance, Sep. 9, 2010.
AU, 2007237096, Apr. 5, 2007, Aerpio Therapeutics, Office Action, Aug. 12, 2011.
AU, 2007237096, Apr. 5, 2007, Aerpio Therapeutics, Response to Office Action, Jun. 12, 2012.
AU, 2007237096, Apr. 5, 2007, Aerpio Therapeutics, Notice of Acceptance, Jul. 19, 2012.
CA, 2,648,284, Apr. 5, 2007, Aerpio Therapeutics, Preliminary Amendment, Jun. 14, 2010.
CA, 2,648,284, Apr. 5, 2007, Aerpio Therapeutics, Office Action, Jan. 17, 2011.
CA, 2,648,284, Apr. 5, 2007, Aerpio Therapeutics, Response to Office Action, May 26, 2011.
CA, 2,648,284, Apr. 5, 2007, Aerpio Therapeutics, Office Action, Nov. 10, 2011.
CA, 2,648,284, Apr. 5, 2007, Aerpio Therapeutics, Response to Office Action, Jan. 16, 2012.
CN, 200780011778.0, Apr. 5, 2007, Aerpio Therapeutics, Office Action, Mar. 21, 2012.
CN, 200780011778.0, Apr. 5, 2007, Aerpio Therapeutics, Response to Office Action, Jul. 15, 2012.
CO, 08105786, Apr. 5, 2007, Aerpio Therapeutics, Examiner's Interview, Jun. 13, 2012.
CO, 08105786, Apr. 5, 2007, Aerpio Therapeutics, Response to Examiner's Interview, Jun. 18, 2012.
IL, 571300, Apr. 5, 2007, Aerpio Therapeutics, Response to Examination Report, May 7, 2011.
IL, 571300, Apr. 5, 2007, Aerpio Therapeutics, Examination Report, May 8, 2012.
IL, 571300, Apr. 5, 2007, Aerpio Therapeutics, Response to Examination Report, Aug. 5, 2012.
JP, 2009-503719, Apr. 5, 2007, Aerpio Therapeutics, Examination Report, Jul. 1, 2011.
JP, 2009-503719, Apr. 5, 2007, Aerpio Therapeutics, Response to Examination Report, Sep. 2, 2011.
JP, 2009-503719, Apr. 5, 2007, Aerpio Therapeutics, Examination Report, Dec. 9, 2011.
JP, 2009-503719, Apr. 5, 2007, Aerpio Therapeutics, Response to Examination Report, Jan. 30, 2012.
JP, 2009-503719, Apr. 5, 2007, Aerpio Therapeutics, Final Rejection, Jun. 28, 2012.
JP, 2009-503719, Apr. 5, 2007, Aerpio Therapeutics, Appeal to Tribunal, Aug. 5, 2012.
KR, 2008-7026944, Apr. 5, 2007, Aerpio Therapeutics, Examination Report, Dec. 20, 2010.
KR, 2008-7026944, Apr. 5, 2007, Aerpio Therapeutics, Response to Examination Report, Dec. 29, 2010.
KR, 2008-7026944, Apr. 5, 2007, Aerpio Therapeutics, Final Examination Report, Aug. 23, 2011.
KR, 2008-7026944, Apr. 5, 2007, Aerpio Therapeutics, Response to Final Examination Report, Sep. 22, 2011.
KR, 2008-7026944, Apr. 5, 2007, Aerpio Therapeutics, Further Response to Final Examination Report, Jul. 9, 2012.
MX, MX/A/2008/012991, Apr. 5, 2007, Aerpio Therapeutics, Examination Report, Sep. 29, 2010.
MX, MX/A/2008/012991, Apr. 5, 2007, Aerpio Therapeutics, Response to Examination Report, Jan. 21, 2011.
MX, MX/A/2008/012991, Apr. 5, 2007, Aerpio Therapeutics, Further Response to Examination Report, Jan. 24, 2011.
MX, MX/A/2008/012991, Apr. 5, 2007, Aerpio Therapeutics, Examination Report, May 25, 2011.
MX, MX/A/2008/012991, Apr. 5, 2007, Aerpio Therapeutics, Response to Examination Report, Aug. 4, 2011.
MX, MX/A/2008/012991, Apr. 5, 2007, Aerpio Therapeutics, Notice of Allowance, Dec. 30, 2011.

NZ, 571300, Apr. 5, 2007, Aerpio Therapeutics, Examination Report, May 21, 2010.

NZ, 571300, Apr. 5, 2007, Aerpio Therapeutics, Response to Examination Report, Jan. 18, 2011.

NZ, 571300, Apr. 5, 2007, Aerpio Therapeutics, Examination Report, May 10, 2011.

NZ, 571300, Apr. 5, 2007, Aerpio Therapeutics, Response to Examination Report, May 25, 2011.

NZ, 571300, Apr. 5, 2007, Aerpio Therapeutics, Examination Report, Aug. 15, 2011.

NZ, 571300, Apr. 5, 2007, Aerpio Therapeutics, Response to Examination Report, Nov. 16, 2011.

RU, 2008138399, Apr. 5, 2007, Aerpio Therapeutics, Restriction Requirement, Oct. 19, 2009.

RU, 2008138399, Apr. 5, 2007, Aerpio Therapeutics, Response to Restriction Requirement, Dec. 23, 2009.

RU, 2008138399, Apr. 5, 2007, Aerpio Therapeutics, Office Action, Feb. 4, 2010.

RU, 2008138399, Apr. 5, 2007, Aerpio Therapeutics, Amendment and Response to Office Action, Jun. 13, 2010.

RU, 2008138399, Apr. 5, 2007, Aerpio Therapeutics, Office Action, Oct. 28, 2010.

RU, 2008138399, Apr. 5, 2007, Aerpio Therapeutics, Amendment and Response to Office Action, Jan. 25, 2011.

RU, 2008138399, Apr. 5, 2007, Aerpio Therapeutics, Office Action, Dec. 2, 2011.

RU, 2008138399, Apr. 5, 2007, Aerpio Therapeutics, Amendment and Response to Office Action, Jan. 12, 1916.

RU, 2008138399, Apr. 5, 2007, Aerpio Therapeutics, Office Action, May 31, 2012.

RU, 2008138399, Apr. 5, 2007, Aerpio Therapeutics, Response to Office Action, Jul. 9, 2012.

VN, 1-2008-02466, Apr. 5, 2007, Aerpio Therapeutics, Office Action, Dec. 12, 2011.

VN, 1-2008-02466, Apr. 5, 2007, Aerpio Therapeutics, Response to Restriction Requirement, Jan. 4, 2012.

Altschul et al., "Gapped BLAST and PSI-BLAST: A New Generation of Protein Database Search Programs," *Nucleic Acids Res.*, 25(27):3389-3402 (1997).

Annex et al., "Growth Factor-Induced Therapeutic Angiogenesis in the Heart: Protein Therapy," *Cardiovascular Research*, 65(3):649-655 (2005).

Ardelt et al., "Estradiol Regulates Angiopoietin-1 mRNA Expression Through Estrogen Receptor-α in a Rodent Experimental Stroke Model," *Stroke*, 36:337-341 (2005).

Auerbach et al., "Angiogenesis Assays: A Critical Overview," *Clinical Chemistry*, 49:32-40 (2003).

Barany et al., "Solid-phase Peptide Synthesis: A Silver Anniversary Report,"*Int. J. Peptide Protein Res.*, 30(6):705-739 (1987).

Bartlett et al., "Molecular Recognition in Chemical and Biological Problems; Cavet: A Program to Facilitate the Structure-Derived Design of Biologically Active Molecules," *Special Pub., Royal Chem. Soc.*, 78:182-196 (1989).

Bohm, "The Computer Program LUDI: A New Method for the De Novo Design of Enzyme Inhibitors," *J. Comuter-Aided. Molec. Design*, 6(1):61-78 (1992).

Bussolino, et al., "Molecular mechanisms of blood vessel formation," *Trends Biochem Sci.* 22(7):251-256 (1997).

Carano et al., "Angiogenesis and Bone Repair," *Drug Discovery Today*, 8(21):980-989 (2003).

Carvalho et al., "The Role of Angiogenesis in a Murine Tibial Model of Distraction Osteogenesis," *Bone*, 34:849-861 (2004).

Chanteau et al., "Synthesis of Anthropomorphic Molecules: The NanoPutians," *J. Org. Chem.*, 68:8750-8766 (2003).

Cohen et al., "Molecular Modeling Software and Methods for Medicinal Chemistry, " *J. Med. Chem.*, 33(3):883-894 (1990).

Daar, "Perspective: Emerging Resistance Profiles of Newly Approved Antiretroviral Drugs," *Topics in HIV Medicine*, 16(4):110-116 (2008).

Dean, "Recent Advances in Drug Design Methods: Where Will They Lead?" *BioEssays*, 16(9):683-687 (1994).

Fachinger et al., "Functional Interaction of Vascular Endothelial-Protein-Tyrosine Phosphatase with the Angiopoietin Receptor Tie-2," *Oncogene*, 18:5948-5953 (1999).

Flower, "Modelling G-Protein-Coupled Receptors for Drug Design," *Biochimica et Biophysica Acta*, 1422:207-234 (1999).

Folkman, J., "Tumor angiogenesis," *The Molecular Basis of Cancer* (eds. Mendelsohn, J., Howley, P. M., Israel, M. A. & Liotta, L. A.) 206-232 (1995).

Gaits et al., "Increase in Receptor-like Protein Tyrosine Phosphatase Activity and Express Level on Density-Dependent Growth Arrest of Endothelial Cells," *Biochem J.*, 311:97-103 (1995).

Goodford, "A Computational Procedure for Determining Energetically Favorable Binding Sites on Biologically Important Macromolecules," *J. Med. Chem.*, 28(7):849-57 (1985).

Goodsell et al., "Automated Docking of Substrates to Proteins by Simulated Annealing," *Proteins Struct. Funct. Genet.* 8:195-202 (1990).

Harder et al., "Characterization and Kinetic Analysis of the Intracellular Domain of Human Protein Tyrosine Phosphatase β (HPTPβ) Using Synthetic Phosphopeptides," *Biochem. J.*, 296:395-401 (1994).

Henikoff et al., "Amino Acid Substitution Matrices from Protein Blocks," *Proc. Natl. Acad. Sci. USA* 89:10915-10919 (1992).

Hopkins et al., "Inhibitors of Kinesin Activity from Structure-Based Computer Screening," *Biochemistry*, 39:2805-2814(2000).

Huang et al., "HCPTPA, a Protein Tyrosine Phosphatase that Regulates Vascular Endothelial Growth Factor Receptor-Mediated Signal Transduction and Biological Activity," *J. Biol. Chem.*, 53:38183-38188 (1999).

Itoh et al., "Purification and Characterization of the Catalytic Domains of the Human Receptor-Linked Protein Tyrosine Phosphatases HPTPβ, Leukocyte Common Antigen (LCA), and Leukocyte Common Antigen-Related Molecule (LAR)," *Journal of Biological Chemistry*, 267(17):12356-12363 (1992).

Jones et al., "Development and Validation of a Genetic Algorithm for Flexible Docking," *J. Mol. Biol.*, 267:727-748 (1997).

Jones et al., "Molecular Recognition of Receptor Sites Using a Genetic Algorithm with a Description of Desolvation," *J. Mol. Biol.*, 245:43-53 (1995).

Keen, "Radioligand Binding Methods for Membrane Preparations and Intact cells," *Methods in Molecular Biology, 83:Receptor Signal Transduction Protocols*, edited Humana Press Inc., Totoway N.J. (1997).

Köhler et al., "Continuous Cultures of Fused Cells Secreting Antibody of Predefined Specificity," *Biotechnology*, 24:524-526 (1992).

Krueger et al., "Structural Diversity and evolution of Human Receptor-Like Protein Tyrosine Phosphatases," *The EMBO Journal*, 9(10):3241-3252 (1990).

Kugathasan et al., "Role of Angiopoietin-1 in Experimental and Human Pulmonary Arterial Hpertension," *Chest*, 128:633-642 (2005).

Kuntz et al., "A Geometric Approach to Macromolecule—Ligand Interactions," *J. Mol. Biol.* 161:269-288 (1982).

Lin et al., "Inhibition of Tumor Angiogenesis Using a Soluble Receptor Establishes a Role for Tie2 in Pathologic Vascular Growth," *J. Clinical Invest.*,100(8):2072-2078 (1997).

Ma et al., "RNase Protection Assay," *Methods*, 10(3):273-8 (1996).

Martin, "3D Database Searching in Drug Design," *J. of Medicinal Chemistry*, 35(12):2145-2154 (1992).

Meadows, "Keeping Up with Drug Safety Information," 2006: *FDA Consumer Magazine*: http://www.fda.gov/fdac/features/2006/306_drugsafety.html, accessed Mar. 17, 2008.

Merrifield, "Solid Phase Peptide Synthesism. I. The Synthesis of a Tetrapeptide," *J. Am. Chem. Soc.*, 85:2149-2154 (1963).

Miranker et al., "Functionality Maps of Binding Sites: A Multiple Copy Simultaneous Search Method," *Proteins: Struc. Func. And Genectics*, 11(1):29-34 (1991).

Navaza, "*AMoRe*: An Automated Package for Molecular Replacement," *J. Acta Cryst.* A50:157-163 (1994).

Nguyen et al., "Cellular Interactions in Vascular Growth and Differentiation," *Int. Rev. Cytol.*, 204:1-48 (2001).

Nishibata et al., "Automatic Creation of Drug Candidate Structures Based on Receptor Structure. Starting Point for Artificial Lead Generation," *Tetrahedron*, 47(43):8985-8990 (1991).

O'Reilly, "Angiostatin: a novel angiogenesis inhibitor that mediates the suppression of metastases by a Lewis lung carcinoma," *Cell*, 79(2):315-28 (1994).

O'Reilly, "Endostatin: an endogenous inhibitor of angiogenesis and tumor growth," *Cell*, 88(2):277-85 (1997).

Rarey et al., "A Fast Flexible Docking Method Using an Incremental Construction Algorithm," *J. Mol. Biol.*, 261:470-489 (1996).

Riechmann et al., "Reshaping Human Antibodies for Therapy," *Nature*, 332:323-327 (1988).

Saliba, "Heparin in the Treatment of Burns: A Review," May 2001; Burn 27(4):349-358; full text edition, pp. 1-16.

Schöneberg et al., "Structural basis of G protein-coupled receptor function," *Molecular and Cellular Endocrinology*, 151:181-193 (1999).

Sexton, "Recent advances in our understanding of peptide hormone receptors and RAMPS," *Current Opinion in Drug Discovery and Development*, 2(5):440-448 (1999).

Shiojima et al., "Disruption of Coordinated Cardiac Hypertrophy and Angiogenesis Contributes to the Transition to Heart Failure," *Journal of Clinical Invest.*, 115(8):2108-2118 (2005).

Shoichet et al., "Lead Discovery Using Molecular Docking," *Chem. Biology*, 6:439-446 (2002).

Siddiqui et al., "Combination of angiopoietin-1 and vascular endothelial growth factor gene therapy enhances arteriogenesis in the ischemic myocardium," *Biochem. Biophys. Res. Comm.*, 310:1002-1009 (2003).

Simons, "Angiogenesis: Where Do We Stand Now?," *Circulation*, 111:1556-1566 (2005).

Simons et al., "Clinical Trials in Coronary Angiogenesis," *Circulation*, 102:73-86 (2000).

Stal et al., "Detailed Analysis of Scoring Functions for Virtual Screening," *J. Med. Chem.*, 44:1035-1042 (2001).

Stetler-Stevenson, "The Role of Matrix Metalloproteinases in Tumor Invasion, Metastasis, and Angiogenesis," *Surg. Oncol. Clin. N. Am.*, 10(2):383-392 (2001).

Suggitt et al., "50 Years of Preclinical Anticancer Drug Screening: Empirical to Target-Drive Approaches," *Clinical Cancer Research*, 11:971-981 (2005).

Suri et al., "Increased Vascularization in Mice Overexpressing Angiopoietin-1," *Science*, 282:468-471 (1998).

Takahashi et al., "Adenoviral-Delivered Angiopoietin-1 Reduces the Infarction and Attenuates the Progression of Cardiace Dysfunction in the Rate Model of Acute Myocardial Infarction," *Molecular Therapy*, 8(4):584-592 (2003).

Teischer, "Potentiation of cytotoxic cancer therapies by TNP-470 alone and with other anti-angiogenic agents," *Int. J. Cancer*, 57(6)920-925 (1994).

Thurston, "Complimentary Actions of VEGF and Angiopoietin-1 on Blood Vessel Growth and Leakage," *J. Anat.*, 200:575-580 (2002).

Thurston et al., "Angiopoietin-1 Protects the Adult Vasculature Against Plasma Leakage," *Nature Medicine*, 6(4):460-463 (2000).

Vailhe et al., "In Vitro Models of Vasculogenesis and Angiogenesis," *Laboratory Investigation*, 81:439-452 (2001).

Wang et al., "Expressions and Characterization of Wild Type, Truncated, and Mutant Forms of the Intracellular Region of the Receptor-Like Protein Tyrosine Phosphatase HPTPβ," *J. of Bio. Chem.*, 267(23):16696-16702 (1992).

Weidner, "Tumor Angiogenesis and Metastasis Correlation in Invasive Breast Carcinoma," *New Eng. J. Med.*, 324(1):108 (1991).

Whitaker et al., "Vascular Endothelial Growth Factor Receptor-2 and Neuropilin-1 Form a Receptor Complex That Is Responsible for the Differential Signaling Potency of $VEGF_{165}$ and $VEGF_{121}$," *Journal of Biological Chemistry*, 276(27):25520-25531 (2001).

Wright et al., "Protein-Tyrosine Phosphatases in the Vessel Wall Differential Expression After Actue Arterial Injury," *Arterioscler Thromb. Vasc.*, 1189-1198 (2000).

Yancopoulos et al., "Vascular-Specific Growth Factors and Blood Vessel Formation," *Nature*, 407(6801):242-248 (2000).

Zhang et al., "Vascular Endothelial Growth Factor and Angiopoietins in Focal Cerebral Ischemia," *Trends Cardiovascular Med.*, 12(2):62-66 (2002).

Collaborative Computational Project, No. 4, "The CCP4 Suite: Programs for Protein Crystallography," *Acta Cryst.*, D50:760-763 (1994).

* cited by examiner

HUMAN PROTEIN TYROSINE PHOSPHATASE INHIBITORS AND METHODS OF USE

PRIORITY

This application is a Continuation Application of U.S. Ser. No. 12/467,430 that was filed on May 18, 2009 now U.S. Pat. No. 8,188,125, which is a Divisional Application of U.S. application Ser. No. 11/821,868, that was filed on Jun. 26, 2007, now U.S. Pat. No. 7,589,212, which application claims the benefit of Provisional Application Ser. No. 60/816,825 that was filed on Jun. 27, 2006, the entirety of each of which applications are incorporated herein by reference.

FIELD

The present disclosure relates to compounds effective as human protein tyrosine phosphatase beta (HPTP-β) inhibitors thereby regulating angiogenesis. The present disclosure further relates to compositions comprising one or more human protein tyrosine phosphatase beta (HPTP-β) inhibitors, and to methods for regulating angiogenesis.

BACKGROUND

Angiogenesis, the sprouting of new blood vessels from the pre-existing vasculature, plays a crucial role in a wide range of physiological and pathological processes (Nguyen, L. L. et al., *Int. Rev. Cytol.*, 204, 1-48, (2001)). Angiogenesis is a complex process, mediated by communication between the endothelial cells that line blood vessels and their surrounding environment. In the early stages of angiogenesis, tissue or tumor cells produce and secrete pro-angiogenic growth factors in response to environmental stimuli such as hypoxia. These factors diffuse to nearby endothelial cells and stimulate receptors that lead to the production and secretion of proteases that degrade the surrounding extracellular matrix. The activated endothelial cells begin to migrate and proliferate into the surrounding tissue toward the source of these growth factors (Bussolino, F., *Trends Biochem. Sci.*, 22, 251-256, (1997)). Endothelial cells then stop proliferating and differentiate into tubular structures, which is the first step in the formation of stable, mature blood vessels. Subsequently, periendothelial cells, such as pericytes and smooth muscle cells, are recruited to the newly formed vessel in a further step toward vessel maturation.

Angiogenesis is regulated by a balance of naturally occurring pro- and anti-angiogenic factors. Vascular endothelial growth factor, fibroblast growth factor, and angiopoeitin represent a few of the many potential pro-angiogenic growth factors. These ligands bind to their respective receptor tyrosine kinases on the endothelial cell surface and transduce signals that promote cell migration and proliferation. Whereas many regulatory factors have been identified, the molecular mechanisms of this process are still not fully understood.

There are many disease states driven by persistent unregulated or improperly regulated angiogenesis. In such disease states, unregulated or improperly regulated angiogenesis may either cause a particular disease or exacerbate an existing pathological condition. For example, ocular neovascularization has been implicated as the most common cause of blindness and underlies the pathology of approximately 20 eye diseases. In certain previously existing conditions such as arthritis, newly formed capillary blood vessels invade the joints and destroy cartilage. In diabetes, new capillaries formed in the retina invade the vitreous humor, causing bleeding and blindness. Both the growth and metastasis of solid tumors are also angiogenesis-dependent (Folkman et al., "Tumor Angiogenesis," Chapter 10, 206-32, in The Molecular Basis of Cancer, Mendelsohn et al., eds., W. B. Saunders, (1995)). It has been shown that tumors which enlarge to greater than 2 mm in diameter must obtain their own blood supply and do so by inducing the growth of new capillary blood vessels. After these new blood vessels become embedded in the tumor, they provide nutrients and growth factors essential for tumor growth as well as a means for tumor cells to enter the circulation and metastasize to distant sites, such as liver, lung or bone (Weidner, *New Eng. J. Med.*, 324, 1, 1-8 (1991)). When used as drugs in tumor-bearing animals, natural inhibitors of angiogenesis may prevent the growth of small tumors (O'Reilly et al., *Cell*, 79, 315-28 (1994)). In some protocols, the application of such inhibitors leads to tumor regression and dormancy even after cessation of treatment (O'Reilly et al., *Cell*, 88, 277-85 (1997)). Moreover, supplying inhibitors of angiogenesis to certain tumors may potentiate their response to other therapeutic regimens (Teischer et al., *Int. J. Cancer*, 57, 920-25 (1994)).

Although many disease states are driven by persistent unregulated or improperly regulated angiogenesis, some disease states could be treated by increased angiogenesis. Tissue growth and repair are biologic events wherein cellular proliferation and angiogenesis occur. Thus an important aspect of wound repair is the revascularization of damaged tissue by angiogenesis.

Chronic, non-healing wounds are a major cause of prolonged morbidity in the aged human population. This is especially the case in bedridden or diabetic patients who develop severe, non-healing skin ulcers. In many of these cases, the delay in healing is a result of inadequate blood supply either as a result of continuous pressure or of vascular blockage. Poor capillary circulation due to small artery atherosclerosis or venous stasis contributes to the failure to repair damaged tissue. Such tissues are often infected with microorganisms that proliferate unchallenged by the innate defense systems of the body which require well vascularized tissue to effectively eliminate pathogenic organisms. As a result, most therapeutic intervention centers on restoring blood flow to ischemic tissues thereby allowing nutrients and immunological factors access to the site of the wound.

Atherosclerotic lesions in large vessels may cause tissue ischemia that could be ameliorated by modulating blood vessel growth to the affected tissue. For example, atherosclerotic lesions in the coronary arteries may cause angina and myocardial infarction that could be prevented if one could restore blood flow by stimulating the growth of collateral arteries. Similarly, atherosclerotic lesions in the large arteries that supply the legs may cause ischemia in the skeletal muscle that limits mobility and in some cases necessitates amputation, which may also be prevented by improving blood flow with angiogenic therapy.

Other diseases such as diabetes and hypertension are characterized by a decrease in the number and density of small blood vessels such as arterioles and capillaries. These small blood vessels are important for the delivery of oxygen and nutrients. A decrease in the number and density of these vessels contributes to the adverse consequences of hypertension and diabetes including claudication, ischemic ulcers, accelerated hypertension, and renal failure. These common disorders and many other less common ailments, such as Burgers disease, could be ameliorated by increasing the number and density of small blood vessels using angiogenic therapy.

It has been suggested that one means for regulating angiogenesis is to treat patients with a human protein tyrosine phosphatase beta (HPTP-β) inhibitor (Kruegar et al., *EMBO J.*, 9, (1990)) and, therefore, to satisfy this need the compounds of the present disclosure have been prepared.

SUMMARY OF THE DISCLOSURE

The compounds of the present disclosure are a new class of compounds that can regulate angiogenesis in humans.

The present disclosure further relates to pharmaceutical compositions and their pharmaceutically acceptable salts, and/or pharmaceutical compositions thereof comprising
   a) an effective amount of one or more compounds according to the present disclosure; and
   b) an excipient.

The present disclosures also relate to methods for controlling angiogenesis, and thereby providing a treatment for diseases affected by angiogenesis, said methods comprising administering to a human an effective amount of a compound according to the present disclosure.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present disclosure.

DETAILED DESCRIPTION OF THE DISCLOSURE

In this specification and in the claims that follow, reference will be made to a number of terms, which shall be defined to have the following meanings:

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "organic unit" as described herein refers to groups or moieties that comprise one or more carbon atoms and which form a portion of one of the compounds or pharmaceutically acceptable salts thereof. For example, many of the substituent units referred to elsewhere herein are organic units. In order to effectively function in the context of their presence in the compounds and/or salts disclosed herein, the organic units should often have variable ranges of restricted size and/or molecular weight, so as to provide desired binding to the target enzymes, solubility, bioabsorption characteristics. For example, organic unit can have, for example, 1-26 carbon atoms, 1-18 carbon atoms, 1-12 carbon atoms, 1-8 carbon atoms, or 1-4 carbon atoms. Organic units often have hydrogen bound to at least some of the carbon atoms of the organic units, and can optionally contain the common heteroatoms found in substituted organic compounds, such as oxygen, nitrogen, sulfur, and the like, or inorganic atoms such as halogens, phosphorus, and the like. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Substituted and unsubstituted linear, branched, or cyclic alkyl units include the following non-limiting examples: methyl ($C_1$), ethyl ($C_2$), n-propyl ($C_3$), iso-propyl ($C_3$), cyclopropyl ($C_3$), n-butyl ($C_4$), sec-butyl ($C_4$), iso-butyl ($C_4$), tert-butyl ($C_4$), cyclobutyl ($C_4$), cyclopentyl ($C_5$), cyclohexyl ($C_6$), and the like; whereas substituted linear, branched, or cyclic alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 2,2,2-trifluoroethyl ($C_3$), 3-carboxypropyl ($C_3$), 2,3-dihydroxycyclobutyl ($C_4$), and the like.

Substituted and unsubstituted linear, branched, or cyclic alkenyl include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.

Substituted and unsubstituted linear or branched alkynyl include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

Substituted and unsubstituted "alkoxy" are used herein denotes a unit having the general formula —$OR^{100}$ wherein $R^{100}$ is an alkyl, alkylenyl, or alkynyl unit as defined herein above, for example, methoxy, methoxymethyl, methoxymethyl.

Substituted and unsubstituted "haloalkyl" are used herein denotes an alkyl unit having a hydrogen atom substituted by one or more halogen atoms, for example, trifluoromethyl, 1,2-dichloroethyl, and 3,3,3-trifluoropropyl.

The term "aryl" as used herein denotes cyclic organic units that comprise at least one benzene ring having a conjugated and aromatic six-membered ring, non-limiting examples of which include phenyl ($C_6$), naphthylen-1-yl ($C_{10}$), naphthylen-2-yl ($C_{10}$). Aryl rings can have one or more hydrogen atoms substituted by another organic or inorganic radical. Non-limiting examples of substituted aryl rings include: 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyanonaphthylen-1-yl ($C_{10}$).

The term "heteroaryl" denotes an organic unit comprising a five or six member conjugated and aromatic ring wherein at least one of the ring atoms is a heteroatom selected from nitrogen, oxygen, or sulfur. The heteroaryl rings can comprise a single ring, for example, a ring having 5 or 6 atoms wherein at least one ring atom is a heteroatom not limited to nitrogen, oxygen, or sulfur, such as a pyridine ring, a furan ring, or thiofuran ring. A "heteroaryl" can also be a fused multicyclic and heteroaromatic ring system having wherein at least one of the rings is an aromatic ring and at least one atom of the aromatic ring is a heteroatom including nitrogen, oxygen, or sulfur The following are non-limiting examples of heteroaryl rings according to the present disclosure:

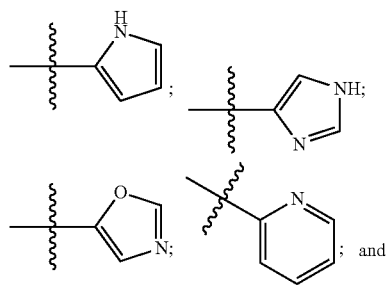

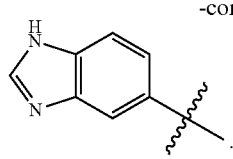

The term "heterocyclic" denotes a ring system having from 3 to 10 atoms wherein at least one of the ring atoms is a heteroatom not limited to nitrogen, oxygen, or sulfur. The rings can be single rings, fused rings, or bicyclic rings. Non-limiting examples of heterocyclic rings include:

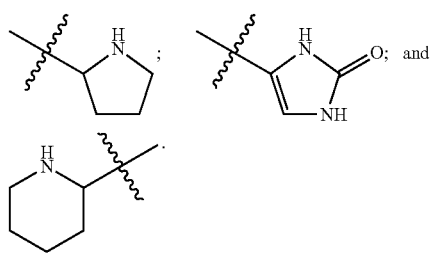

All of the aforementioned heteroaryl or heterocyclic rings can be optionally substituted with one or more substitutes for hydrogen as described herein further.

Throughout the description of the present disclosure the terms having the spelling "thiophene-2-yl and thiophene-3-yl" are used to describe the heteroaryl units having the respective formulae:

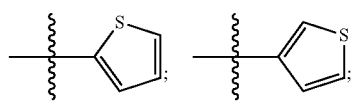

whereas in naming the compounds of the present disclosure, the chemical nomenclature for these moieties are typically spelled "thiophen-2-yl and thiophen-3-yl" respectively. Herein the terms "thiophene-2-yl and thiophene-3-yl" are used when describing these rings as units or moieties which make up the compounds of the present disclosure solely to make it unambiguous to the artisan of ordinary skill which rings are referred to herein.

The following are non-limiting examples of units that can substitute for hydrogen atoms:

i) $C_1$-$C_{12}$ linear, branched, or cyclic alkyl, alkenyl, and alkynyl; for example, methyl ($C_1$), ethyl ($C_2$), ethenyl ($C_2$), ethynyl ($C_2$), n-propyl ($C_3$), iso-propyl ($C_3$), cyclopropyl ($C_3$), 3-propenyl ($C_3$), 1-propenyl (also 2-methylethenyl) ($C_3$), isopropenyl (also 2-methylethen-2-yl) ($C_3$), prop-2-ynyl (also propargyl) ($C_3$), propyn-1-yl ($C_3$), n-butyl ($C_4$), sec-butyl ($C_4$), iso-butyl ($C_4$), tert-butyl ($C_4$), cyclobutyl ($C_4$), buten-4-yl ($C_4$), cyclopentyl ($C_5$), cyclohexyl ($C_6$);

ii) substituted or unsubstituted $C_6$ or $C_{10}$ aryl; for example, phenyl, naphthyl (also referred to herein as naphthylen-1-yl ($C_{10}$) or naphthylen-2-yl ($C_{10}$));

iii) substituted or unsubstituted $C_1$-$C_9$ heterocyclic rings; as described herein below;

iv) substituted or unsubstituted $C_1$-$C_9$ heteroaryl rings; as described herein below;

v) —(CR$^{12a}$R$^{12b}$)$_z$OR$^{11}$; for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;

vi) —(CR$^{12a}$R$^{12b}$)$_z$C(O)R$^{11}$; for example, —COCH$_3$, —CH$_2$COCH$_3$, —OCH$_2$CH$_3$, —CH$_2$COCH$_2$CH$_3$, —COCH$_2$CH$_2$CH$_3$, and —CH$_2$COCH$_2$CH$_2$CH$_3$;

vii) —(CR$^{12a}$R$^{12b}$)$_z$C(O)OR$^{11}$; for example, —CO$_2$CH$_3$, —CH$_2$CO$_2$CH$_3$, —CO$_2$CH$_2$CH$_3$, —CH$_2$CO$_2$CH$_2$CH$_3$, —CO$_2$CH$_2$CH$_2$CH$_3$, and —CH$_2$CO$_2$CH$_2$CH$_2$CH$_3$;

viii) (CR$^{12a}$R$^{12b}$)$_z$C(O)N(R$^{11}$)$_2$; for example, —CONH$_2$, —CH$_2$CONH$_2$, —CONHCH$_3$, —CH$_2$CONHCH$_3$, —CON(CH$_3$)$_2$, and —CH$_2$CON(CH$_3$)$_2$;

ix) —(CR$^{12a}$R$^{12b}$)$_z$(R$^{11}$)$_2$; for example, —NH$_2$, —CH$_2$NH$_2$, —NHCH$_3$, —N(CH$_3$)$_2$, —NH(CH$_2$CH$_3$), —CH$_2$NHCH$_3$, —CH$_2$N(CH$_3$)$_2$, and —CH$_2$NH(CH$_2$CH$_3$);

x) halogen; —F, —Cl, —Br, and —I;

xi) —(CR$^{12a}$R$^{12b}$)$_z$CN;

xii) —(CR$^{12a}$R$^{12b}$)$_z$NO$_2$;

xiii) —CH$_j$X$_k$; wherein X is halogen, j is from 0 to 2, j+k=3; for example, —CH$_2$F, —CHF$_2$, —CF$_3$, —CCl$_3$, or —CBr$_3$;

xiv) —(CR$^{12a}$R$^{12b}$)$_z$SR$^{11}$; —SH, —CH$_2$SH, —SCH$_3$, —CH$_2$SCH$_3$, —SC$_6$H$_5$, and —CH$_2$SC$_6$H$_5$;

xv) —(CR$^{12a}$R$^{12b}$)$_z$SO$_2$R$^{11}$; —CH$_2$SO$_2$H, —SO$_2$CH$_3$, —CH$_2$SO$_2$CH$_3$, —SO$_2$C$_6$H$_5$, and —CH$_2$SO$_2$C$_6$H$_5$; and xiii) —(CR$^{12a}$R$^{12b}$)$_z$SO$_3$R$^{11}$; for example, —SO$_3$H, —CH$_2$SO$_3$H, —SO$_3$CH$_3$, —CH$_2$SO$_3$CH$_3$, —SO$_3$C$_6$H$_5$, and —CH$_2$SO$_3$C$_6$H$_5$;

wherein each R$^{13}$ is independently hydrogen, substituted or unsubstituted C$_1$-C$_4$ linear, branched, or cyclic alkyl, phenyl, benzyl; or two R$^{13}$ units can be taken together to form a ring comprising 3-7 atoms; R$^{14a}$ and R$^{14b}$ are each independently hydrogen or C$_1$-C$_4$ linear or branched alkyl; the index p is from 0 to 4.

For the purposes of the present disclosure the terms "compound," "analog," and "composition of matter" stand equally well for the phenylsulfamic acids described herein, including all enantiomeric forms, diastereomeric forms, salts, and the like, and the terms "compound," "analog," and "composition of matter" are used interchangeably throughout the present specification.

The present disclosure addresses a major unmet medical need, inter alia; providing compositions of effective human protein tyrosine phosphatase beta (HPTP-β) inhibitors; and thereby provide a means for regulating angiogenesis and blood vessel remodeling in disorders wherein angiogenesis is decreased or where tissue blood flow is insufficient or where increased blood flow would be beneficial.

This and other unmet medical needs are resolved by the human protein tyrosine phosphatase beta (HPTP-β) inhibitors of the present disclosure, which are capable of regulating angiogenesis and blood vessel remodeling and thereby serve as a means for treating diseases which are caused by insufficient regulation of human protein tyrosine phosphatase beta (HPTP-β).

The compounds disclosed herein include all pharmaceutically acceptable salt forms, for example, salts of both basic groups, inter alia, amines, as well as salts of acidic groups, inter alia, sulfamic acids, and carboxylic acids. The following are non-limiting examples of anions that can form salts with basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: sodium, lithium, potassium, calcium, magnesium, bismuth, and the like.

R Units

R is a unit chosen from:

i) hydrogen;

ii) substituted or unsubstituted phenyl; and iii) substituted or unsubstituted heteroaryl ring.

One example of R relates to compounds wherein R is hydrogen, said compounds having the general formula:

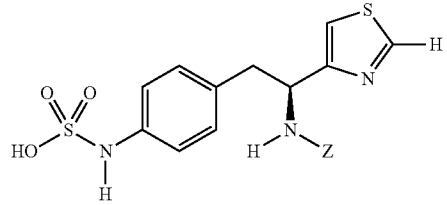

wherein Z is further defined herein below.

Another example of the compounds of Formula (I) includes compounds wherein R is phenyl or substituted phenyl, said compounds having the general formula:

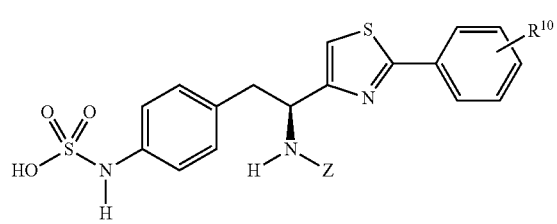

wherein R$^{10}$ represents one or more optional replacements for hydrogen.

The following are non-limiting examples of R$^{10}$ units that can substitute for hydrogen atoms on a phenyl unit:

i) C$_1$-C$_{12}$ linear, branched, or cyclic alkyl, alkenyl, and alkynyl; for example, methyl (C$_1$), ethyl (C$_2$), ethenyl (C$_2$), ethynyl (C$_2$), n-propyl (C$_3$), iso-propyl (C$_3$), cyclopropyl (C$_3$), 3-propenyl (C$_3$), 1-propenyl (also 2-methylethenyl) (C$_3$), isopropenyl (also 2-methylethen-2-yl) (C$_3$), prop-2-ynyl (also propargyl) (C$_3$), propyn-1-yl (C$_3$), n-butyl (C$_4$), sec-butyl (C$_4$), iso-butyl (C$_4$), tert-butyl (C$_4$), cyclobutyl (C$_4$), buten-4-yl (C$_4$), cyclopentyl (C$_5$), cyclohexyl (C$_6$);

ii) substituted or unsubstituted C$_6$ or C$_{10}$ aryl; for example, phenyl, naphthyl (also referred to herein as naphthylen-1-yl (C$_{10}$) or naphthylen-2-yl (C$_{10}$));

iii) substituted or unsubstituted C$_1$-C$_9$ heterocyclic rings; as described herein below;

iv) substituted or unsubstituted C$_1$-C$_9$ heteroaryl rings; as described herein below;

v) —(CR$^{12a}$R$^{12b}$)$_z$OR$^{11}$; for example, —OH, —CH$_2$OH, —OCH$_3$, —CH$_2$OCH$_3$, —OCH$_2$CH$_3$, —CH$_2$OCH$_2$CH$_3$, —OCH$_2$CH$_2$CH$_3$, and —CH$_2$OCH$_2$CH$_2$CH$_3$;

vi) —(CR$^{12a}$R$^{12b}$)$_z$C(O)R$^{11}$; for example, —COCH$_3$, —CH$_2$COCH$_3$, —OCH$_2$CH$_3$, —CH$_2$COCH$_2$CH$_3$, —COCH$_2$CH$_2$CH$_3$, and —CH$_2$COCH$_2$CH$_2$CH$_3$;

vii) —(CR$^{12a}$R$^{12b}$)$_z$C(O)OR$^{11}$; for example, —CO$_2$CH$_3$, —CH$_2$CO$_2$CH$_3$, —CO$_2$CH$_2$CH$_3$, —CH$_2$CO$_2$CH$_2$CH$_3$, —CO$_2$CH$_2$CH$_2$CH$_3$, and —CH$_2$CO$_2$CH$_2$CH$_2$CH$_3$;

viii) $(CR^{12a}R^{12b})_zC(O)N(R^{11})_2$; for example, —CONH₂, —CH₂CONH₂, —CONHCH₃, —CH₂CONHCH₃, —CON(CH₃)₂, and —CH₂CON(CH₃)₂;

x) halogen; —F, —Cl, —Br, and —I;

xi) —$(CR^{12a}R^{12b})_zCN$;

xii) —$(CR^{12a}R^{12b})_zNO_2$;

xiii) —$CH_jX_k$; wherein X is halogen, j is from 0 to 2, j+k=3; for example, —CH₂F, —CHF₂, —CF₃, —CCl₃, or —CBr₃;

xiv) —$(CR^{12a}R^{12b})_zSR^{11}$; —SH, —CH₂SH, —SCH₃, —CH₂SCH₃, —SC₆H₅, and —CH₂SC₆H₅;

xv) —$(CR^{12a}R^{12b})_zSO_2R^{11}$; —CH₂SO₂H, —SO₂CH₃, —CH₂SO₂CH₃, —SO₂C₆H₅, and —CH₂SO₂C₆H₅; and xiii) —$(CR^{12a}R^{12b})_zSO_3R^{11}$; for example, —SO₃H, —CH₂SO₃H, —SO₃CH₃, —CH₂SO₃CH₃, —SO₃C₆H₅, and —CH₂SO₃C₆H₅;

wherein each $R^{13}$ is independently hydrogen, substituted or unsubstituted $C_1$-$C_4$ linear, branched, or cyclic alkyl, phenyl, benzyl; or two $R^{13}$ units can be taken together to form a ring comprising 3-7 atoms; $R^{14a}$ and $R^{14b}$ are each independently hydrogen or $C_1$-$C_4$ linear or branched alkyl; the index p is from 0 to 4.

Another example of the compounds of Formula (I) includes compounds wherein R is a substituted or unsubstituted heteroaryl ring. For the purposes of the present disclosure the following are non-limiting examples of heteroaryl rings suitable as R units for the compounds of the present disclosure: 1,2,3,4-tetrazolyl; [1,2,3]triazolyl; imidazolyl; pyrrolyl; oxazolyl; isoxazolyl; [1,2,4]oxadiazolyl; [1,3,4] oxadiazolyl; furanyl; thiopheneyl; isothiazolyl; thiazolyl; [1,2,4]thiadiazolyl; and [1,3,4]thiadiazolyl.

The heteroaryl units that comprise R units can be substituted by one or more units chosen from methyl, ethyl, n-propyl, iso-propyl, cyclopropyl, n-butyl, sec-butyl, iso-butyl, tert-butyl, cyclopropylmethyl, methoxy, ethoxy, n-propoxy, iso-propoxy, cyclopropoxy, n-butoxy, sec-butoxy, iso-butoxy, tert-butoxy, cyclopropoxy, fluoro, chloro, fluoromethyl, difluoromethyl, and trifluoromethyl.

An example of the compounds of Formula (I) includes compounds wherein R units include units having the formulae:

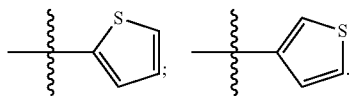

Another example of the compounds of Formula (I) includes compounds wherein R units include units having the formulae:

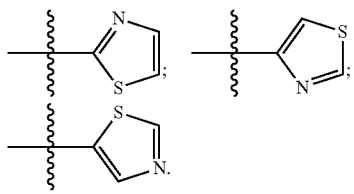

A further example of the compounds of Formula (I) includes compounds wherein R units include units having the formulae:

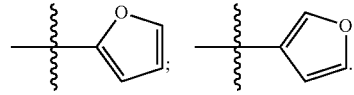

Z is a substituted or unsubstituted [1,3,4]thiadiazol-2-yl unit having the formula:

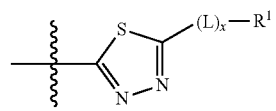

and $R^1$ is a substituent group that can be independently chosen from a wide variety of inorganic (hydrogen, hydroxyl, amino, halogen or the like) or organic substituent units, such as alkyls, cycloalkyls, heterocyclic, heteroaryls, and the like, wherein such substituent units can optionally have from 1 to 12 carbon atoms, or 1 to 10 carbon atoms, or 1 to six carbon atoms. In many aspects of the invention $R^1$ is chosen from:

i) hydrogen;

ii) substituted or unsubstituted $C_1$-$C_6$ linear, branched, or cyclic alkyl;

iii) substituted or unsubstituted $C_6$ or $C_{10}$ aryl;

iv) —$OR^4$;

v) —$C(O)OR^5$;

vi) —$COR^6$; and vii) —$NR^7C(O)OR^8$;

$R^4$ is hydrogen or substituted or unsubstituted $C_1$-$C_6$ linear, branched, or cyclic alkyl; $R^5$ is $C_1$-$C_6$ linear or branched alkyl, or benzyl; $R^6$ is $C_1$-$C_6$ linear, branched, or cyclic alkyl, or phenyl; $R^7$ is hydrogen or methyl; $R^8$ is $C_1$-$C_6$ linear or branched alkyl, or benzyl.

One example of compounds according to Formula (I) includes an $R^1$ unit that is hydrogen thereby providing compounds having the general formula:

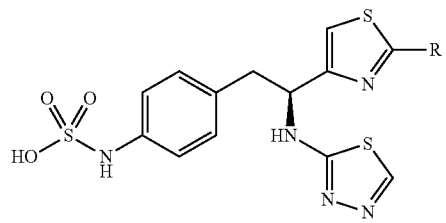

wherein R is defined herein above.

Another example of compounds according to Formula (I) includes compounds wherein $R^1$ is substituted or unsubstituted $C_1$-$C_6$ linear, branched, or cyclic alkyl, non-limiting examples of which include $R^1$ units chosen from methyl, ethyl, n-propyl, iso-propyl, cyclopropyl, n-butyl, sec-butyl, iso-butyl, tert-butyl, and cyclopropylmethyl.

A further example of compounds according to Formula (I) includes compounds wherein $R^1$ is a substituted or unsubstituted $C_6$ or $C_{10}$ aryl unit, i.e. phenyl, naphthylen-1-yl, and naphthylen-2-yl. Non-limiting examples of this aspect include phenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-ethylphenyl, 3-ethylphenyl, 4-ethylphenyl, 2-isopropylphenyl, 3-isopropylphenyl, 4-isopropylphenyl, 2-cyanophenyl, 3-cyanophenyl, 4-cyanophenyl, 2-nitrophenyl, 3-nitrophenyl, 4-nitrophenyl, 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino) phenyl, 3-(N,N-dimethylamino)phenyl, 3-(N-ethylamino) phenyl, 3-(N,N-diethylamino)phenyl, 4-aminophenyl, 4-(N-methylamino)phenyl, 4-(N,N-dimethylamino)phenyl, 4-(N-ethylamino)phenyl, 4-(N,N-diethylamino)phenyl, naphthylen-1-yl, and naphthylen-2-yl A yet further example of compounds according to Formula (I) includes compounds wherein $R^1$ has the formula —$NR^7C(O)OR^8$; $R^7$ is hydrogen and $R^8$ is chosen from methyl ($C_1$), ethyl ($C_2$), n-propyl ($C_3$), iso-propyl ($C_3$), and cyclopropyl ($C_3$).

The Z units of the present disclosure can further comprise a linking unit L, which when present, serves to connect the [1,3,4]thiadiazol-2-yl unit to the $R^1$ unit. When the index x is equal to 0, the linking unit is absent. When the index x is equal to 1 the linking unit is present.

L is a linking unit having the formula:

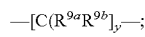

wherein $R^{9a}$ and $R^{9b}$ are each independently hydrogen, $C_1$-$C_6$ linear or branched alkyl, or phenyl and the index y is from 1 to 4.

One example of L units includes units wherein $R^{9a}$ and $R^{9b}$ are each hydrogen and the index y is equal to 1, these units have the formula:

that is also referred to herein as methylene linking units.

Another example of L units includes units wherein all $R^{9a}$ and $R^{9b}$ units are hydrogen and the index y is equal to 2, this unit has the formula:

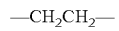

and is also referred to herein as an ethylene linking unit.

A described herein above the compounds of the present invention includes all pharmaceutically acceptable salt forms. A compound having the formula:

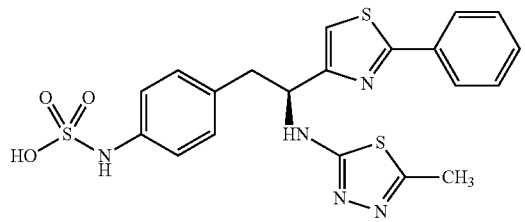

can form salts, for example, a salt of the sulfonic acid:

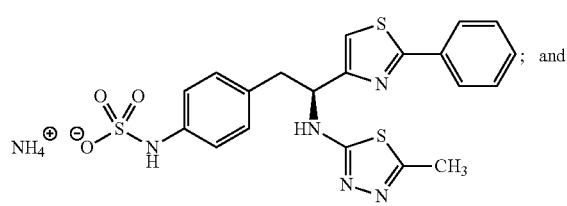

; and

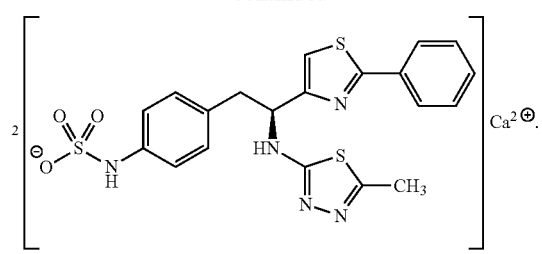

The compounds can also exist in a zwitterionic form, for example:

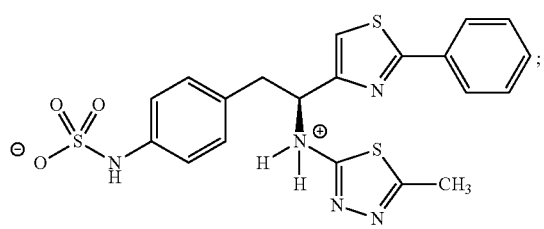

or
as a salt of a strong acid, for example:

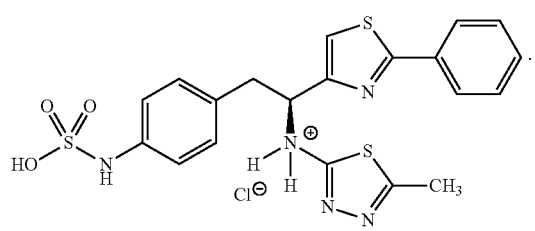

The analogs (compounds) of the present disclosure are arranged into several categories to assist the formulator in applying a rational synthetic strategy for the preparation of analogs which are not expressly exampled herein. The arrangement into categories does not imply increased or decreased efficacy for any of the compositions of matter described herein.

The compounds of the present disclosure can be prepared using the procedure outlined herein below in steps (a)-(f) or by making modifications thereof which are known to those skilled in the art and by which can be accomplished without the need for undue experimentation.

Step (a)

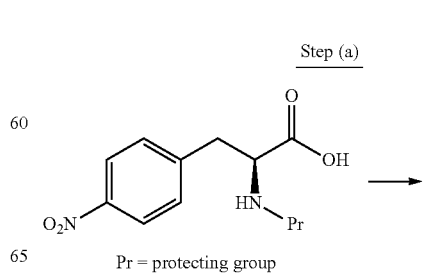

Pr = protecting group

13
-continued
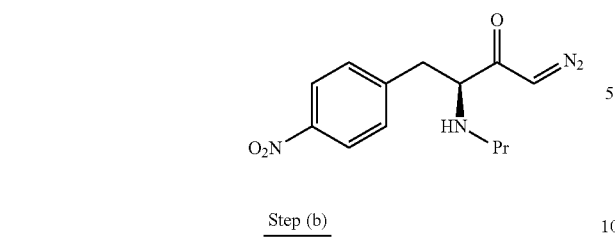
Step (b)
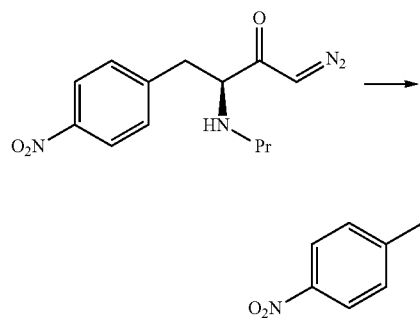
Step (c)
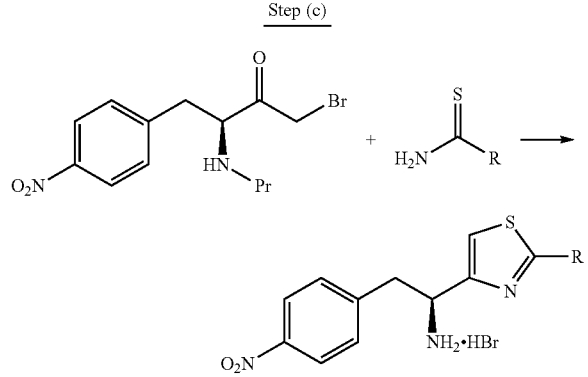
Step (d)
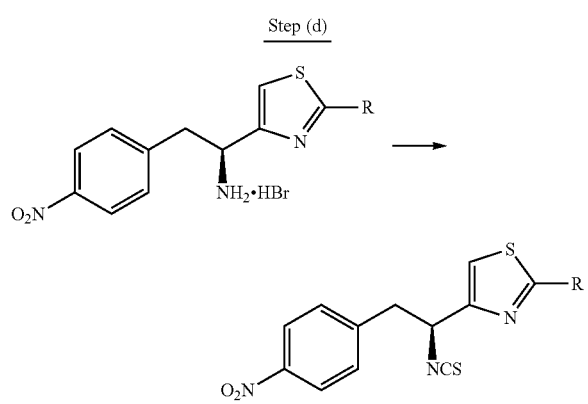
Step (e)
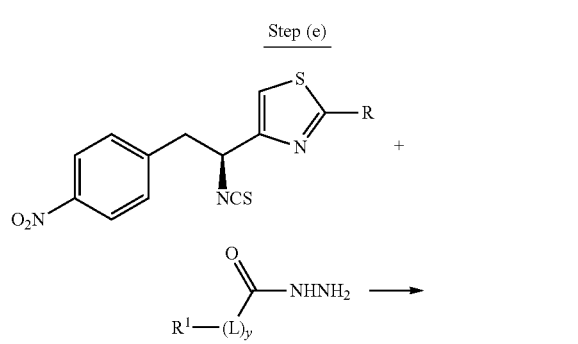
14
-continued
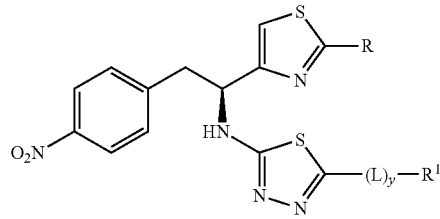
Step (f)
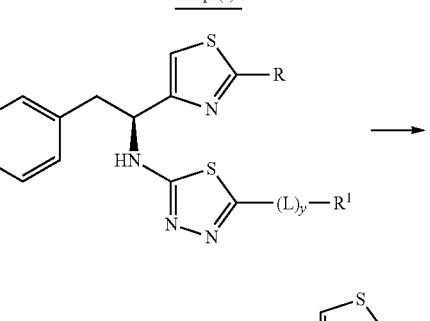
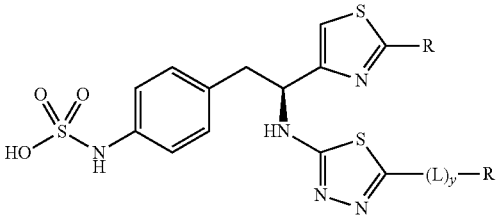
Scheme I herein below outlines the procedure for preparing the analogs of the present disclosure that is described in detail in Example 1.
Scheme I
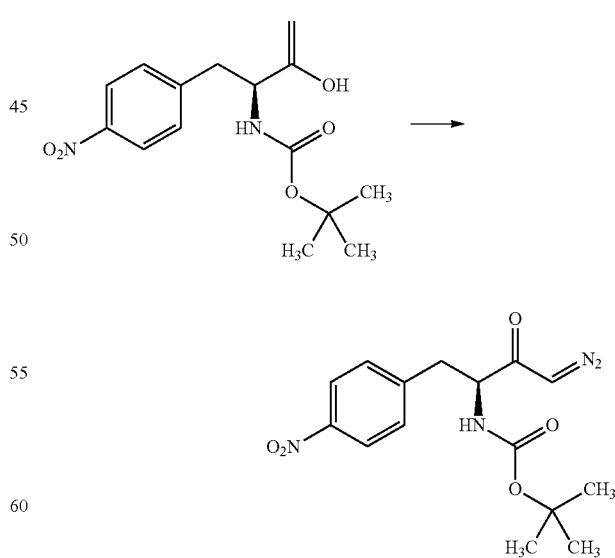
1
Reagents and conditions: (a) (i) (iso-butyl)OCOCl, Et₃N, THF; 0° C., 20 min.
(ii) CH₂N₂; 0° C. to room temp for 3 hours.

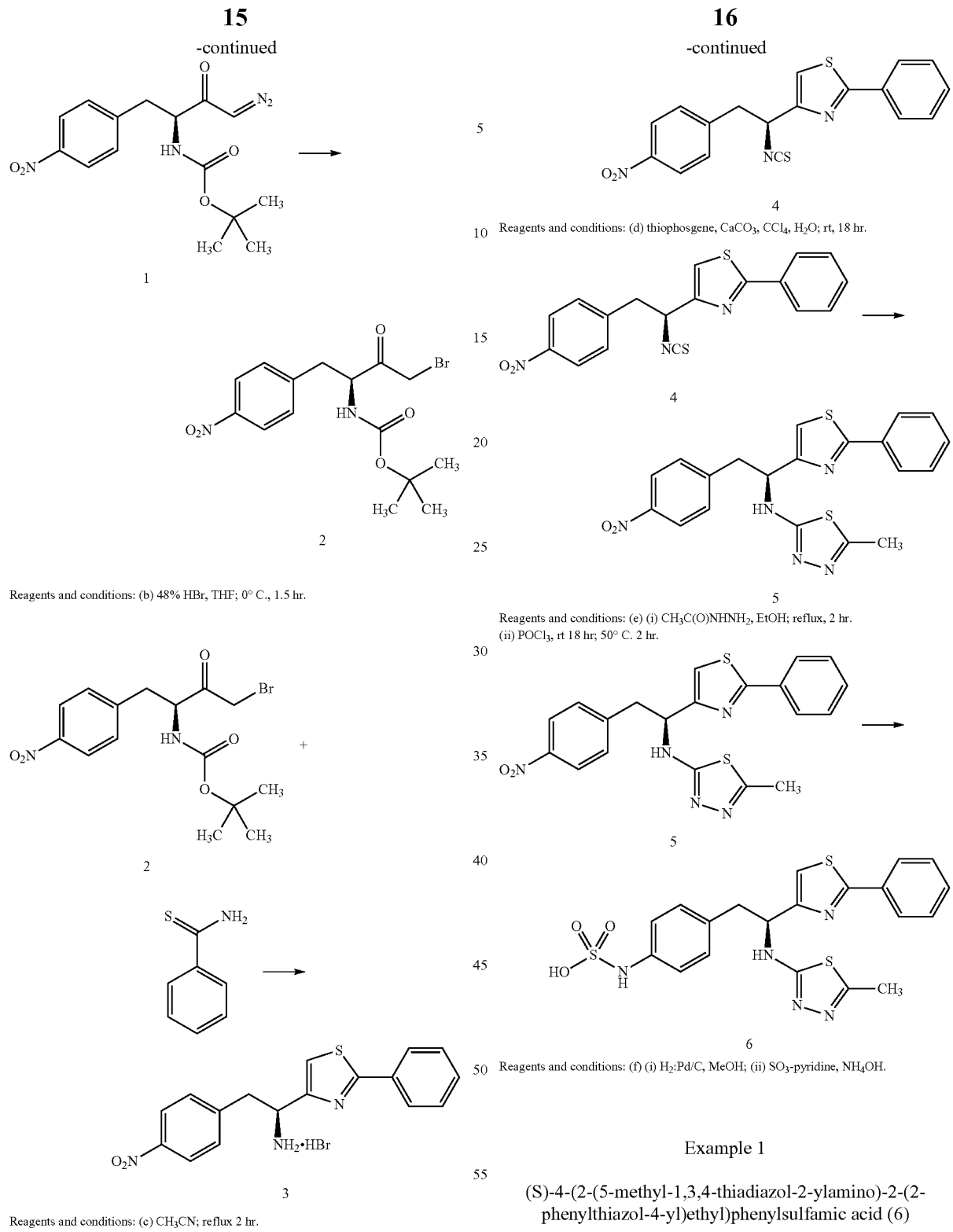

Reagents and conditions: (b) 48% HBr, THF; 0° C., 1.5 hr.

Reagents and conditions: (c) CH3CN; reflux 2 hr.

Reagents and conditions: (d) thiophosgene, CaCO3, CCl4, H2O; rt, 18 hr.

Reagents and conditions: (e) (i) CH3C(O)NHNH2, EtOH; reflux, 2 hr.
(ii) POCl3, rt 18 hr; 50° C. 2 hr.

Reagents and conditions: (f) (i) H2:Pd/C, MeOH; (ii) SO3-pyridine, NH4OH.

Example 1

(S)-4-(2-(5-methyl-1,3,4-thiadiazol-2-ylamino)-2-(2-phenylthiazol-4-yl)ethyl)phenylsulfamic acid (6)

Preparation of [3-diazo-1-(4-nitrobenzyl)-2-oxo-propyl]-carbamic acid tert-butyl ester (1): To a 0° C. solution of 2-(S)-tert-butoxycarbonylamino-3-(4-nitrophenyl)-propionic acid (1.20 g, 4.0 mmol) in THF (20 mL) is added dropwise triethylamine (0.61 mL, 4.4 mmol) followed by iso-butyl chloroformate (0.57 mL, 4.4 mmol). The reaction mixture is stirred at 0° C. for 20 min and filtered. The filtrate is treated with an ether solution of diazomethane (~16 mmol) at 0° C. The reaction mixture is stirred at room temperature for 3 hours and concentrated. The residue is dissolved in EtOAc and washed successively with water and brine, dried ($Na_2SO_4$), filtered and concentrated in vacuo. The resulting residue is purified over silica (hexane/EtOAc 2:1) to afford 1.1 g (82% yield) of the desired product as a slightly yellow solid. $^1$H NMR (300 MHz, $CDCl_3$) δ 8.16 (d, J=8.7 Hz, 2H), 7.39 (d, J=8.7 Hz, 2H), 5.39 (s, 1H), 5.16 (d, J=6.3 Hz, 1H), 4.49 (s, 1H), 3.25 (dd, J=13.8 and 6.6, 1H), 3.06 (dd, J=13.5 and 6.9 Hz, 1H), 1.41 (s, 9H).

Preparation of [3-bromo-1-(4-nitro-benzyl)-2-oxo-propyl]-carbamic acid tert-butyl ester (2): To a 0° C. solution of [3-diazo-1-(4-nitrobenzyl)-2-oxo-propyl]-carbamic acid tert-butyl ester, 1, (0.350 g, 1.04 mmol) in THF (5 mL) is added dropwise 48% aq. HBr (0.14 mL, 1.25 mmol). The reaction mixture is stirred at 0° C. for 1.5 hours and quenched at 0° C. with sat.$Na_2CO_3$. The mixture is extracted with EtOAc (3×25 mL) and the combined organic extracts are washed with brine, dried ($Na_2SO_4$), filtered and concentrated in vacuo to afford 0.400 g of the desired product which is used in the next step without further purification. $^1$H NMR (300 MHz, $CDCl_3$) δ 8.20 (d, J=8.4 Hz, 2H), 7.39 (d, J=8.4 Hz, 2H), 5.06 (d, J=7.8 Hz, 1H), 4.80 (q, J=6.3 Hz, 1H), 4.04 (s, 2H), 1.42 (s, 9H).

Preparation of (S)-2-(4-nitrophenyl)-1-(2-phenylthiazol-4-yl)ethanamine hydrobromide salt (3): A mixture of [3-bromo-1-(4-nitro-benzyl)-2-oxo-propyl]-carbamic acid-tert-butyl ester, 2, (1.62 g, 4.17 mmol) and benzothioamide (0.630 g, 4.59 mmol), in $CH_3CN$ (5 mL) is refluxed for 24 hours. The reaction mixture is cooled to room temperature and diethyl ether (50 mL) is added to the solution and the precipitate which forms is collected by filtration. The solid is dried under vacuum to afford 1.059 g (63%) of the desired product. ESI+MS 326 (M+1).

Preparation of (S)-4-(1-isothiocyanato-2-(4-nitrophenyl)ethyl)-2-phenylthiazole (4): To a solution of (S)-2-(4-nitrophenyl)-1-(2-phenylthiazol-4-yl)ethanamine hydrobromide salt, 3, (2.03 g, 5 mmol) and $CaCO_3$ (1 g, 10 mmol) in $CCl_4$/water (10:7.5 mL) is added thiophosgene (0.46 mL, 6 mmol). The reaction is stirred at room temperature for 18 hours then diluted with $CH_2Cl_2$ and water. The layers are separated and the aqueous layer extracted with $CH_2Cl_2$. The combined organic layers are washed with brine, dried ($Na_2SO_4$) and concentrated in vacuo to a residue which is purified over silica ($CH_2Cl_2$) to afford 1.71 g (93%) of the desired product. ESI+MS 368 (M+1).

Preparation of (S)-5-methyl-N-(2-(4-nitrophenyl)-1-(2-phenylthiazol-4-yl)ethyl)-1,3,4-thiadiazol-2-amine (5): A solution of (S)-4-(1-isothiocyanato-2-(4-nitrophenyl)-ethyl)-2-phenylthiazole, 4, (332 mg, 0.876 mmol) and acetic hydrazide (65 mg, 0.876 mmol) in EtOH (5 mL) is refluxed for 2 hours. The solvent is removed under reduced pressure, the residue is dissolved in $POCl_3$ (3 mL) and the resulting solution is stirred at room temperature for 18 hours after which the solution is heated to 50° C. for 2 hours. The solvent is removed in vacuo and the residue is dissolved in EtOAc (40 mL) and the resulting solution is treated with 1N NaOH until the pH remains approximately 8. The solution is extracted with EtOAc. The combined aqueous layers are washed with EtOAc, the organic layers combined, washed with brine, dried over $MgSO_4$, filtered, and concentrated in vacuo to afford 0.345 g (93%) of the desired product as a yellow solid. $^1$H NMR ($CDCl_3$) 8.09 (d, J=8.4 Hz, 2H), 7.91 (m, 2H), 7.46 (m, 4H), 7.44 (s, 1H), 5.23 (m, 1H), 3.59 (m, 2H), 2.49 (s, 3H). ESI+MS 424 (M+1).

Preparation of (S)-4-(2-(5-methyl-1,3,4-thiadiazol-2-ylamino)-2-(2-phenylthiazol-4-yl)ethyl)phenylsulfamic acid (6): (S)-5-Methyl-N-(2-(4-nitrophenyl)-1-(2-phenylthiazol-4-yl)ethyl)-1,3,4-thiadiazol-2-amine, 5, (0.404 g, 0.954 mmol) is dissolved in MeOH (5 mL). Pd/C (50 mg, 10% w/w) is added and the mixture is stirred under a hydrogen atmosphere until the reaction is judged to be complete. The reaction mixture is filtered through a bed of CELITE™ and the solvent removed under reduced pressure. The crude product is dissolved in pyridine (4 mL) and treated with $SO_3$-pyridine (0.304 g, 1.91 mmol). The reaction is stirred at room temperature for 5 minutes after which a 7% solution of $NH_4OH$ (50 mL) is added. The mixture is then concentrated and the resulting residue is purified by reverse phase preparative HPLC to afford 0.052 g (11% yield) of the desired product as the ammonium salt. $^1$H ($CD_3OD$): δ 8.00-7.97 (m, 2H), 7.51-7.47 (m, 3H), 7.23 (s, 1H), 7.11-7.04 (q, 4H, J=9.0 Hz), 5.18 (t, 1H, J=7.2 Hz), 3.34-3.22 (m, 2H), 2.50 (s, 3H). ESI−MS 472 (M−1).

The following is a general procedure for isolating the final compound as a free acid.

Reduction of the aryl nitro group to free a amine.

To a Parr hydrogenation vessel is charged the nitro compound [for example, intermediate 5] (1.0 eq) and Pd/C (10% Pd on C, 50% wet, Degussa-type E101 NE/W, 2.68 g, 15 wt %) as solids. MeOH (15 mL/g) is added to provide a suspension. The vessel is put on a Parr hydrogenation apparatus. The vessel is submitted to a fill/vacuum evacuate process with $N_2$ (3×20 psi) to inert, followed by the same procedure with $H_2$ (3×40 psi). The vessel is filled with $H_2$ and the vessel is shaken under 40 psi $H_2$ for ~40 hr. The vessel is evacuated and the atmosphere is purged with $N_2$ (5×20 psi). An aliquot is filtered and analyzed by HPLC to insure complete conversion. The suspension is filtered through a pad of celite to remove the catalyst, and the homogeneous yellow filtrate is concentrated by rotary evaporation to afford the desired product which is used without further purification.

Preparation of free sulfamic acid: A 100 mL RBF is charged with the free amine (1.0 eq) prepared in the step described herein above. Acetonitrile (5 mL/g) is added and the yellow suspension which is typically yellow to orange in color is stirred at room temperature. A second 3-necked 500 mL RBF is charged with $SO_3$.pyr (1.4 eq) and acetonitrile (5 mL/g) and the suspension is stirred at room temperature. Both suspensions are gently heated until the reaction solution containing the amine becomes orange to red-orange in color (typically at about 40-45° C.). This substrate containing solution is poured in one portion into the stirring suspension of $SO_3$.pyr at 35° C. The resulting opaque mixture is stirred vigorously while allowed to slowly cool to room temperature. After stirring for 45 min, or once the reaction is determined to be complete by HPLC, water (20 mL/g) is added to the colored suspension to provide a homogeneous solution having a pH of approximately 2.4. Concentrated $H_3PO_4$ is added slowly to lower the pH to approximately 1.4. During this pH adjustment, an off-white precipitate typically forms and the solution is stirred at room temperature for an additional hour. The suspension is filtered and the filter cake is washed with the filtrate. The filter cake is air-dried overnight to afford the desired product as the free acid.

The following are non-limiting examples of compounds according to the present disclosure.

(S)-4-(2-(5-Phenyl-1,3,4-thiadiazol-2-ylamino)-2-(2-phenylthiazol-4-yl)ethyl)-phenylsulfamic acid: $^1$H ($CD_3OD$): δ 7.97-7.94 (m, 2H), 7.73-7.70 (m, 2H), 7.44-7.39 (m, 6H), 7.25 (s, 1H), 7.12 (s, 4H), 5.29 (t, 1H, J=6.9 Hz), 3.35-3.26 (m, 2H).

4-((S)-2-(5-Propyl-1,3,4-thiadiazol-2-ylamino)-2-(2-(thiophen-2-yl)thiazol-4-yl)ethyl)phenylsulfamic acid: $^1$H ($CD_3OD$): δ 7.59-7.54 (m, 2H), 7.17-7.03 (m, 6H), 5.13 (t, 1H, J=7.2 Hz), 3.32-3.13 (m, 2H), 2.81 (t, 2H, J=7.4 Hz), 1.76-1.63 (h, 6H, J=7.4 Hz), 0.97 (t, 3H, J=7.3 Hz).

4-((S)-2-(5-Benzyl-1,3,4-thiadiazol-2-ylamino)-2-(2-(thiophen-2-yl)thiazol-4-yl)ethyl)phenylsulfamic acid: $^1$H (CD$_3$OD): δ (m, 2H), 7.49-7.45 (m, 2H), 7.26-7.16 (m, 5H), 7.05-6.94 (m, 6H), 5.04 (t, 1H, J=7.1 Hz), 4.07 (s, 2H), 3.22-3.04 (m, 2H).

5-(3-Methoxybenzyl)-N4S)-2-(4-nitrophenyl)-1-(2-(thiophen-2-yl)thiazol-4-yl)ethyl)-1,3,4-thiadiazol-2-amine: $^1$H (CD$_3$OD): δ 7.68-7.64 (m, 2H), 7.33 (t, 1H, J=8.6 Hz), 7.23-7.12 (m, 6H), 6.94-6.91 (m, 3H), 5.22 (t, 1H, J=7.1 Hz), 4.22 (s, 2H), 3.86 (s, 3H), 3.40-3.26 (m, 2H).

4-((S)-2-(5-(Naphthalen-1-ylmethyl)-1,3,4-thiadiazol-2-ylamino)-2-(2-(thiophen-2-yl)thiazol-4-yl)ethyl)phenylsulfamic acid: $^1$H (CD$_3$OD): δ 8.08-8.05 (m, 1H), 7.89-7.80 (m, 2H), 7.55-7.43 (m, 6H), 7.11-7.00 (m, 6H), 5.08 (t, 1H, J=7.1 Hz), 4.63 (s, 2H), 3.26-3.08 (m, 2H).

4-((S)-2-(5-((Methoxycarbonyl)methyl)-1,3,4-thiadiazol-2-ylamino)-2-(2-(thiophen-2-yl)thiazol-4-yl)ethyl)phenylsulfamic acid: $^1$H (CD$_3$OD): δ 7.48-7.44 (m, 2H), 7.03-6.92 (m, 6H), 5.02 (t, 1H, J=7.2 Hz), 4.30 (s, 2H), 3.55 (s, 3H), 3.22-3.02 (m, 2H).

4-((S)-2-(5-((2-Methylthiazol-4-yl)methyl)-1,3,4-thiadiazol-2-ylamino)-2-(2-(thiophen-2-yl)thiazol-4-yl)ethyl)phenylsulfamic acid: $^1$H (CD$_3$OD): δ 7.60-7.56 (m, 2H), 7.19 (s, 1H), 7.15-7.12 (m, 2H), 7.09-7.03 (q, 4H, J=8.7 Hz), 5.14 (t, 1H, J=7.2 Hz), 4.28 (s, 2H), 3.33-3.14 (m, 2H), 2.67 (s, 3H).

Inhibition of HPTP-β provides a means for enhancing the activity of endothelial receptor tyrosine kinases including, but not limited to, angiopoietin receptor tyrosine kinase, Tie-2, and the VEGF receptor tyrosine kinase, VEGFR2, and thereby treat disease states wherein tissue blood flow is insufficient. The compounds of the present disclosure serve as a means for providing regulation of angiogenesis and other activities of endothelial receptor tyrosine kinases. As such the present disclosure addresses a major unmet medical need, inter alia;

Providing compositions of effective human protein tyrosine phosphatase beta (HPTP-β) inhibitors; and thereby provide a means for regulating angiogenesis, blood vessel remodeling and other activities of endothelial receptor tyrosine kinases in disorders wherein where tissue blood flow is insufficient or where increased blood flow would be beneficial. The effect of human protein tyrosine phosphatase inhibitors has been shown to affect several human disease conditions or disorders, these disorders include, but are not limited to;

i) Peripheral Artery Disease—Shiojima, I. et al., *Journal of Clinical Invest.*, 115, 3108-2118, (2005);
ii) Coronary Artery Disease—Siddiqui, A. J. et al., *Biochem. Biophys. Res. Comm.*, 310, 1002-1009, (2003);
iii) Myocardial Infarction (Acute Coronary Syndrome)—Takahashi, K. et al., *Molecular Therapy*, 8, 584-592, (2003);
iv) Stroke (Cerebral Vascular Disease)—Stewart, D. et al., *Chest*, 128, 633-642, (2005);
v) Heart Failure—Thurston G., *J. Anat.*, 200, 575-580, (2002);
vi) Hypertension—Caravalho, R. S. et al., *Bone*, 34, 849-861, (2004);
vii) Diabetic and Ischemic Neuropathy—Carano, A. D. and Filvaroff, E. H., *Drug Discovery Today*, 8, 980-989, (2003);
viii) Wound Healing and Skin Aging—Simons, M., *Circulation*, 111, 1556-1566 (2005);
xi) Vascular Inflammation and atherosclerosis—Annex, B. H. and Simons M., *Cardiovascular Research*, 65, 649-655, (2005);
x) Vascular Leak Syndromes—Ardelt, A. A. et al., *Stroke*, 36, 337-341 (2005); and
xi) Bone Growth, Maintenance and Repair—*Cardiovascular Medicine*, 12, 62-66, (2002).

Formulations

The present disclosure also relates to compositions or formulations which comprise the HPTPβ inhibitors according to the present disclosure. In general, the compositions of the present disclosure comprise:
a) an effective amount of one or more phenylsufamic acids and salts thereof according to the present disclosure which are effective as human protein tyrosine phosphatase beta (HPTP-β) inhibitors; and
b) one or more excipients.

For the purposes of the present disclosure the term "excipient" and "carrier" are used interchangeably throughout the description of the present disclosure and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present disclosure have improved cellular potency, pharmacokinetic properties, as well as improved oral bioavailability.

Non-limiting examples of compositions according to the present disclosure include:
a) from about 0.001 mg to about 1000 mg of one or more phenylsulfamic acids according to the present disclosure; and
b) one or more excipients.

Another embodiment according to the present disclosure relates to the following compositions:
a) from about 0.01 mg to about 100 mg of one or more phenylsulfamic acids according to the present disclosure; and
b) one or more excipients.

A further embodiment according to the present disclosure relates to the following compositions:
a) from about 0.1 mg to about 10 mg of one or more phenylsulfamic acids according to the present disclosure; and
b) one or more excipients.

The term "effective amount" as used herein means "an amount of one or more phenylsulfamic acids, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. Thus, it is not possible to specify an exact "effective amount." For example, several divided doses may be administered daily or the dose may be proportionally reduced as indicated by the exigencies of the therapeutic situation. In addition, the compositions of the present disclosure can be administered as frequently as necessary to achieve a therapeutic amount.

Method of Use

The present disclosure relates to methods for regulating angiogenesis in a human comprising administering to a human a compound according to the present disclosure as described herein.

One embodiment of the methods of the present disclosure relates to a method for treating a disorder in a subject wherein tissue blood flow reserve is insufficient and chosen from, but not limited to, coronary artery disease, peripheral vascular disease or cerebral vascular disease.

A second embodiment of the methods of the present disclosure relates to a method of vascularizing ischemic tissue. As used herein, "ischemic tissue," means tissue that is deprived of adequate blood flow. Examples of ischemic tissue include, but are not limited to, tissue that lack adequate blood supply resulting from myocardial and cerebral infarctions, mesenteric or limb ischemia, or the result of a vascular occlusion or stenosis. In one example, the interruption of the supply of oxygenated blood may be caused by a vascular occlusion. Such vascular occlusion may be caused by arteriosclerosis, trauma, surgical procedures, disease, and/or other etiologies. Also included within the methods of treatment of the present disclosure is the treatment of skeletal muscle and myocardial ischemia, stroke, coronary artery disease, peripheral vascular disease, coronary artery disease.

A third embodiment of the methods of the present disclosure relates to a method of repairing tissue. As used herein, "repairing tissue" means promoting tissue repair, regeneration, growth, and/or maintenance including, but not limited to, wound repair or tissue engineering. One skilled in the art appreciates that new blood vessel formation is required for tissue repair. In turn, tissue may be damaged by, including, but not limited to, traumatic injuries or conditions including arthritis, osteoporosis and other skeletal disorders, and burns. Tissue may also be damaged by injuries due to surgical procedures, irradiation, laceration, toxic chemicals, viral or bacterial infections, or burns. Tissue in need of repair also includes non-healing wounds. Examples of non-healing wounds include non-healing skin ulcers resulting from diabetic pathology; or fractures that do not heal readily.

The compounds of the present disclosure are also suitable for use in effecting tissue repair in the context of guided tissue regeneration (GTR) procedures. Such procedures are currently used by those skilled in the arts to accelerate wound healing following invasive surgical procedures.

A fourth embodiment of the methods of the present disclosure relates to a method of promoting tissue repair characterized by enhanced tissue growth during the process of tissue engineering. As used herein, "tissue engineering" is defined as the creation, design, and fabrication of biological prosthetic devices, in combination with synthetic or natural materials, for the augmentation or replacement of body tissues and organs. Thus, the present methods may be used to augment the design and growth of human tissues outside the body for later implantation in the repair or replacement of diseased tissues. For example, antibodies may be useful in promoting the growth of skin graft replacements that are used as a therapy in the treatment of burns.

A further iteration of the tissue engineering embodiment of the methods of the present disclosure includes in cell-containing or cell-free devices that induce the regeneration of functional human tissues when implanted at a site that requires regeneration. As discussed herein, biomaterial-guided tissue regeneration may be used to promote bone regrowth in, for example, periodontal disease. Thus, antibodies may be used to promote the growth of reconstituted tissues assembled into three-dimensional configurations at the site of a wound or other tissue in need of such repair.

A yet further iteration of the tissue engineering embodiment of the methods of the present disclosure, the compounds described herein may be included in external or internal devices containing human tissues designed to replace the function of diseased internal tissues. This approach involves isolating cells from the body, placing them with structural matrices, and implanting the new system inside the body or using the system outside the body. For example, antibodies may be included in a cell-lined vascular graft to promote the growth of the cells contained in the graft. It is envisioned that the methods of the disclosure may be used to augment tissue repair, regeneration and engineering in products such as cartilage and bone, central nervous system tissues, muscle, liver, and pancreatic islet (insulin-producing) cells.

The present disclosure also relates to the use of the phenylsulfamic acids according to the present disclosure in the manufacture of a medicament for promoting the growth of skin graft replacements.

The present disclosure also relates to the use of the phenylsulfamic acids according to the present disclosure in the manufacture of a medicament for use in effecting tissue repair in the context of guided tissue regeneration (GTR) procedures.

The compounds of the present disclosure can be used in the manufacture of one or more medicaments, non-limiting examples of which are:

A compound for use in the manufacture of a medicament useful for the purposes of tissue engineering thereby affecting enhanced tissue growth.

A compound for use in the manufacture of a medicament for the treatment of an ischemic disorder in a subject.

Procedures

Screening Assays Using In Vitro and In Vivo Models of Angiogenesis

Compounds of the disclosure may be screened in angiogenesis assays that are known in the art. Such assays include in vitro assays that measure surrogates of blood vessel growth in cultured cells or formation of vascular structures from tissue explants and in vivo assays that measure blood vessel growth directly or indirectly (Auerbach, R., et al. (2003). Clin Chem 49, 32-40, Vailhe, B., et al. (2001). Lab Invest 81, 439-452).

1. In Vitro Models of Angiogenesis

The in vitro models which are suitable for use in the present disclosure employ cultured endothelial cells or tissue explants and measure the effect of agents on "angiogenic" cell responses or on the formation of blood capillary-like structures. Non-limiting examples of in vitro angiogenesis assays include but are not limited to endothelial cell migration and proliferation, capillary tube formation, endothelial sprouting, the aortic ring explant assay and the chick aortic arch assay.

2. In Vivo Models of Angiogenesis

The in vivo agents or antibodies which are suitable for use in the present disclosure are administered locally or systemically in the presence or absence of growth factors (i.e. VEGF or angiopoietin 1) and new blood vessel growth is measured by direct observation or by measuring a surrogate marker such as hemoglobin content or a fluorescent indicator. Non-limiting examples of in vitro angiogenesis assays include but are not limited to chick chorioallantoic membrane assay, the corneal angiogenesis assay, and the MATRIGEL™ plug assay.

3. Procedures for Determining Vascularization of Ischemic Tissue

Standard routine techniques are available to determine if a tissue is at risk of suffering ischemic damage from undesirable vascular occlusion. For example, in myocardial disease these methods include a variety of imaging techniques (e.g., radiotracer methodologies, x-ray, and MRI) and physiological tests. Therefore, induction of angiogenesis as an effective means of preventing or attenuating ischemia in tissues affected by or at risk of being affected by a vascular occlusion can be readily determined.

A person skilled in the art of using standard techniques may measure the vascularization of tissue. Non-limiting examples of measuring vascularization in a subject include SPECT (single photon emission computed tomography); PET (positron emission tomography); MRI (magnetic resonance imaging); and combination thereof, by measuring blood flow to tissue before and after treatment. Angiography may be used as an assessment of macroscopic vascularity. Histologic evaluation may be used to quantify vascularity at the small vessel level. These and other techniques are discussed in Simons, et al., "Clinical trials in coronary angiogenesis," *Circulation,* 102, 73-86 (2000).

The following are non-limiting examples of HPTPβ (IC$_{50}$ µM) and PTP1B (IC$_{50}$ µM) activity is listed herein below in Table I.

TABLE I

| Compound | HPTPβ IC$_{50}$ µM | PTP1B IC$_{50}$ µM |
|---|---|---|
| (S)-4-(2-(5-methyl-1,3,4-thiadiazol-2-ylamino)-2-(2-phenylthiazol-4-yl)ethyl)phenylsulfamic acid | 0.003 | 1.4 |
| (S)-4-(2-(5-Phenyl-1,3,4-thiadiazol-2-ylamino)-2-(2-phenylthiazol-4-yl)ethyl)-phenylsulfamic acid | 0.046 | 3.7 |
| 4-((S)-2-(5-Propyl-1,3,4-thiadiazol-2-ylamino)-2-(2-(thiophen-2-yl)thiazol-4-yl)ethyl)phenylsulfamic acid | 0.0002 | 4.71 |
| 4-((S)-2-(5-Benzyl-1,3,4-thiadiazol-2-ylamino)-2-(2-(thiophen-2-yl)thiazol-4-yl)ethyl)phenylsulfamic acid | 0.0006 | 3.86 |
| 4-((S)-2-(5-((Methoxycarbonyl)methyl)-1,3,4-thiadiazol-2-ylamino)-2-(2-(thiophen-2-yl)thiazol-4-yl)ethyl)phenylsulfamic acid | 0.002 | 1.55 |
| 4-((S)-2-(5-((2-Methylthiazol-4-yl)methyl)-1,3,4-thiadiazol-2-ylamino)-2-(2-(thiophen-2-yl)thiazol-4-yl)ethyl)phenylsulfamic acid | 9 × 10$^{-6}$ | 0.58 |

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A compound having the formula:

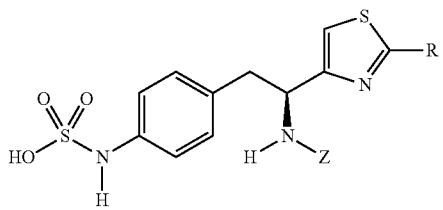

wherein R is a unit chosen from:
i) hydrogen;
ii) substituted or unsubstituted phenyl; and
iii) substituted or unsubstituted heteroaryl ring;
Z is a substituted or unsubstituted [1,3,4]thiadiazol-2-yl unit having the formula:

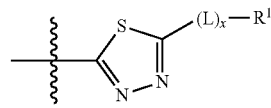

$R^1$ is chosen from:
i) hydrogen;
ii) substituted or unsubstituted $C_1$-$C_6$ linear, $C_3$-$C_6$ branched, or $C_3$-$C_6$ cyclic alkyl;
iii) substituted or unsubstituted $C_6$ or $C_{10}$ aryl;
iv) —OR$^4$;
v) —C(O)OR$^5$;
vi) —COR$^6$;
vii) —NR$^7$C(O)OR$^8$; and
viii) substituted or unsubstituted heteroaryl;
$R^4$ is hydrogen or substituted or unsubstituted $C_1$-$C_6$ linear, $C_3$-$C_6$ branched, or $C_3$-$C_6$ cyclic alkyl; $R^5$ is $C_1$-$C_6$ linear or $C_3$-$C_6$ branched alkyl, or benzyl; $R^6$ is $C_1$-$C_6$ linear, $C_3$-$C_6$ branched, or $C_3$-$C_6$ cyclic alkyl, or phenyl; $R^7$ is hydrogen or methyl; $R^8$ is $C_1$-$C_6$ linear or $C_3$-$C_6$ branched alkyl, or benzyl;

L is a unit having the formula —[C(R$^{9a}$R$^{9b}$)]$_y$—;
$R^{9a}$ and $R^{9b}$ are each independently hydrogen, $C_1$-$C_6$ linear or $C_3$-$C_6$ branched alkyl, or phenyl; and
the index x is 0 or 1; the index y is from 1 to 4;
or a pharmaceutically acceptable salt thereof.

2. The compound according to claim 1, wherein the compound is a salt comprising anions chosen from chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, and citrate.

3. The compound according to claim 1, wherein the compound is a salt comprising cations chosen from ammonium, sodium, lithium, potassium, calcium, magnesium, and bismuth.

4. The compound according to claim 1, wherein R is phenyl.

5. The compound according to claim 1, wherein R is a heteroaryl unit chosen from 1,2,3,4-tetrazol-1-yl, 1,2,3,4-tetrazol-5-yl, [1,2,3]triazol-4-yl, [1,2,3]triazol-5-yl, [1,2,4]triazol-4-yl, [1,2,4]triazol-5-yl, imidazol-2-yl, imidazol-4-yl, pyrrol-2-yl, pyrrol-3-yl, oxazol-2-yl, oxazol-4-yl, oxazol-5-yl, isoxazol-3-yl, isoxazol-4-yl, isoxazol-5-yl, [1,2,4]oxadiazol-3-yl, [1,2,4]oxadiazol-5-yl, [1,3,4]oxadiazol-2-yl, furan-2-yl, furan-3-yl, thiophen-2-yl, thiophen-3-yl, isothiazol-3-yl, isothiazol-4-yl, isothiazol-5-yl, thiazol-2-yl, thiazol-4-yl, thiazol-5-yl, [1,2,4]thiadiazol-3-yl, [1,2,4]thiadiazol-5-yl, and [1,3,4]thiadiazol-2-yl.

6. The compound according to claim 1, wherein R is thiophen-2-yl or thiophen-3-yl.

7. The compound according to claim 1, wherein $R^1$ is chosen from methyl, ethyl, n-propyl, iso-propyl, cyclopropyl, n-butyl, sec-butyl, iso-butyl, tert-butyl, and cyclopropylmethyl.

8. The compound according to claim 1, wherein L has the formula —$CH_2$—.

9. The compound according to claim 8, wherein $R^1$ is chosen from substituted or unsubstituted phenyl, naphthalen-1-yl, and thiazol-4-yl, said substitutions chosen from methyl, ethyl, n-propyl, hydroxy, hydroxymethyl, methoxy, fluoro, chloro, and trifluoromethyl.

10. A compound according to claim 9, wherein $R^1$ is chosen from phenyl, naphthalen-1-yl, 3-methoxyphenyl, and 2-methylthiazol-4-yl.

11. A composition comprising:
A) one or more compounds according to claim 1; and
B) one or more excipients or carriers.

* * * * *